US009561215B2

(12) United States Patent
Li et al.

(10) Patent No.: US 9,561,215 B2
(45) Date of Patent: Feb. 7, 2017

(54) BAX-ACTIVATING CANCER THERAPEUTICS

(71) Applicant: The University of Louisville Research Foundation Inc., Louisville, KY (US)

(72) Inventors: Chi Li, Prospect, KY (US); John O. Trent, Louisville, KY (US)

(73) Assignee: THE UNIVERSITY OF LOUISVILLE RESEARCH FOUNDATION INC., Louisville, KY (US)

( * ) Notice: Subject to any disclaimer, the term of this patent is extended or adjusted under 35 U.S.C. 154(b) by 132 days.

(21) Appl. No.: 14/589,050

(22) Filed: Jan. 5, 2015

(65) Prior Publication Data

US 2015/0190379 A1  Jul. 9, 2015

Related U.S. Application Data

(60) Provisional application No. 61/923,437, filed on Jan. 3, 2014.

(51) Int. Cl.
*A61K 31/437* (2006.01)
*A61K 31/282* (2006.01)
*A61K 31/495* (2006.01)

(52) U.S. Cl.
CPC .......... *A61K 31/437* (2013.01); *A61K 31/282* (2013.01); *A61K 31/495* (2013.01)

(58) Field of Classification Search
None
See application file for complete search history.

(56) References Cited

PUBLICATIONS

J. M. Adams and S. Cory "Bcl-2-regulated apoptosis: mechanism and therapeutic potential." Curr.Opin.Immunol. 19:488-496 (2007).
C. G. Azzoli et al., "Cisplatin versus carboplatin for patients with metastatic non-small-cell lung cancer—an old rivalry renewed." J.Natl.Cancer Inst. 99:828-829 (2007).
S. Bleicken et al., "Molecular details of Bax activation, oligomerization, and membrane insertion." J.Biol.Chem. 285:6636-6647 (2010).
P. Bose et al., "Bax expression measured by AQUAnalysis is an independent prognostic marker in oral squamous cell carcinoma." BMC.Cancer 12:332 (2012).
M. Certo et al., "Mitochondria primed by death signals determine cellular addiction to antiapoptotic BCL-2 family members." Cancer Cell 9:351-365 (2006).
J. E. Chipuk and D. R. Green "How do BCL-2 proteins induce mitochondrial outer membrane permeabilization?" Trends Cell Biol. 18:157-164 (2008).
Chou, T. C. "Drug combination studies and their synergy quantification using the Chou-Talalay method." Cancer Res. 70:440-446 (2010).

P. E. Czabotar et al., "Bax crystal structures reveal how BH3 domains activate Bax and nucleate its oligomerization to induce apoptosis." Cell 152:519-531 (2013).
N. N. Danial and S. J. Korsmeyer "Cell death: critical control points." Cell 116:205-219 (2004).
S. J. Dawson et al., "BCL2 in breast cancer: a favourable prognostic marker across molecular subtypes and independent of adjuvant therapy received." Br.J.Cancer 103:668-675 (2010).
G. Dewson et al., "Bax dimerizes via a symmetric BH3:groove interface during apoptosis." Cell Death.Differ. 19:661-670 (2012).
G. I. Evan and K. H. Vousden "Proliferation, cell cycle and apoptosis in cancer." Nature 411:342-348 (2001).
S. W. Fesik "Promoting apoptosis as a strategy for cancer drug discovery." Nat.Rev.Cancer 5:876-885 (2005).
E. Gavathiotis "Direct and selective small-molecule activation of proapoptotic BAX." Nat.Chem.Biol. 8:639-645 (2012).
E. Gavathiotis et al., "BAX activation is initiated at a novel interaction site." Nature 455:1076-1081 (2008).
F. Grange et al., "Bcl-2 protein expression is the strongest independent prognostic factor of survival in primary cutaneous large B-cell lymphomas." Blood 103:3662-3668 (2004).
D. Hanahan and R. A. Weinberg "Hallmarks of cancer: the next generation." Cell 144:646-674 (2011).
J. M. Hardwick and R. J. Youle "SnapShot: BCL-2 proteins." Cell 138:404, 404 (2009).
W. G. Kaelin, Jr. "The concept of synthetic lethality in the context of anticancer therapy." Nat.Rev.Cancer 5:689-698 (2005).
C. T. Keith, A. A. Borisy, and B. R. Stockwell "Multicomponent therapeutics for networked systems." Nat.Rev.Drug Discov. 4:71-78 (2005).
H. Kim et al., "Hierarchical regulation of mitochondrion-dependent apoptosis by BCL-2 subfamilies." Nat.Cell Biol. 8:1348-1358 (2006).
H. Kim et al., "Stepwise activation of BAX and BAK by tBID, BIM, and PUMA initiates mitochondrial apoptosis." Mol. Cell 36:487-499 (2009).
T. Kuwana et al., "Bid, Bax, and lipids cooperate to form supramolecular openings in the outer mitochondrial membrane." Cell 111:331-342 (2002).

(Continued)

*Primary Examiner* — Jeffrey H Murray
(74) *Attorney, Agent, or Firm* — Thrive IP; Jeremy M. Stipkala

(57) ABSTRACT

The pro-apoptotic Bcl-2 protein Bax initiates apoptosis in almost all apoptotic paradigms. Agents facilitating disruptive Bax insertion into mitochondrial membranes have potential as cancer therapeutics. Small molecule compounds associating with the hydrophobic groove of the pro-apoptotic Bcl-2 protein Bax have been identified and found to promote Bax-dependent, but not Bak-dependent, apoptosis. The compounds alter Bax protein stability in vitro and promote Bax insertion into mitochondria, leading to Bax-dependent mitochondrial outer membrane permeabilization and apoptosis. The compounds activating the pro-apoptotic Bcl-2 protein Bax inhibit the growth of tumors by inducing apoptosis. Pharmaceutical compositions comprising the compounds that activate Bax and induce Bax-dependent apoptosis are useful as anti-cancer therapeutic agents alone or with other anti-cancer agents. Methods for inducing apoptosis and for treating cancer involve administering the compounds to a patient in need thereof.

7 Claims, 20 Drawing Sheets

(56) References Cited

PUBLICATIONS

J. M. Lambert et al., "PRIMA-1 reactivates mutant p53 by covalent binding to the core domain." Cancer Cell 15:376-388 (2009).

A. Letai "BCL-2: found bound and drugged!" Trends Mol.Med. 11:442-444 (2005).

A. Letai "Puma strikes Bax." J.Cell Biol. 185:189-191 (2009).

T. Lindsten et al., "The combined functions of proapoptotic Bcl-2 family members bak and bax are essential for normal development of multiple tissues." Mol.Cell 6:1389-1399 (2000).

J. F. Lovell et al., "Membrane binding by tBid initiates an ordered series of events culminating in membrane permeabilization by Bax." Cell 135:1074-1084 (2008).

M. Nguyen et al., "Small molecule obatoclax (GX15-070) antagonizes MCL-1 and overcomes MCL-1-mediated resistance to apoptosis." Proc.Natl.Acad.Sci.U.S.A 104:19512-19517 (2007).

C. T. Ni et al., "Pretreatment mitochondrial priming correlates with clinical response to cytotoxic chemotherapy." Science 334:1129-1133 (2011).

F. H. Niesen, H. Berglund, and M. Vedadi "The use of differential scanning fluorimetry to detect ligand interactions that promote protein stability." Nat.Protoc. 2:2212-2221 (2007).

K. E. Olberding et al., "Actinomycin D synergistically enhances the efficacy of the BH3 mimetic: ABT-737 by downregulating Mcl-1 expression." Cancer Biol.Ther. 10:918-929 (2010).

T. Oltersdorf et al., "An inhibitor of Bcl-2 family proteins induces regression of solid tumours." Nature 435:677-681 (2005).

A. Pozzan "Molecular descriptors and methods for ligand based virtual high throughput screening in drug discovery." Curr.Pharm. Des 12:2099-2110 (2006).

J. A. Ryan, J. K. Brunelle, and A. Letai "Heightened mitochondrial priming is the basis for apoptotic hypersensitivity of CD4+ CD8+ thymocytes." Proc.Natl.Acad.Sci.U.S.A 107:12895-12900 (2010).

K. Soejima, W. Fang, and B. J. Rollins "DNA methyltransferase 3b contributes to oncogenic transformation induced by SV40T antigen and activated Ras." Oncogene 22:4723-4733 (2003).

M. L. Stewart, E. Fire, A. E. Keating, and L. D. Walensky "The MCL-1 BH3 helix is an exclusive MCL-1 inhibitor and apoptosis sensitizer." Nat.Chem.Biol. 6:595-601 (2010).

M. Suzuki, R. J. Youle, and N. Tjandra "Structure of Bax: coregulation of dimer formation and intracellular localization." Cell 103:645-654 (2000).

M. Vogler, D. Dinsdale, M. J. Dyer, and G. M. Cohen "Bcl-2 inhibitors: small molecules with a big impact on cancer therapy." Cell Death.Differ. 16:360-367 (2009).

L. D. Walensky and E. Gavathiotis "BAX unleashed: the biochemical transformation of an inactive cytosolic monomer into a toxic mitochondrial pore." Trends Biochem.Sci. 36:642-652 (2011).

G. Wang et al., "Structure-based design of potent small-molecule inhibitors of anti-apoptotic Bcl-2 proteins." J.Med. Chem. 49:6139-6142 (2006).

X. Wang et al., "Bcl-2 proteins regulate ER membrane permeability to luminal proteins during ER stress-induced apoptosis." Cell Death.Differ. 18:38-47 (2011).

M. C. Wei et al., "Proapoptotic BAX and BAK: a requisite gateway to mitochondrial dysfunction and death." Science 292:727-730 (2001).

J. A. Wells and C. L. McClendon "Reaching for high-hanging fruit in drug discovery at protein-protein interfaces." Nature 450:1001-1009 (2007).

C. White et al., "The endoplasmic reticulum gateway to apoptosis by Bcl-X(L) modulation of the InsP3R." Nat.Cell Biol. 7:1021-1028 (2005).

N. Xiros et al., "Carboplatin plus gemcitabine in patients with inoperable or metastatic pancreatic cancer: a phase II multicenter study by the Hellenic Cooperative Oncology Group." Ann.Oncol. 16:773-779 (2005).

K. W. Yip and J. C. Reed "Bcl-2 family proteins and cancer." Oncogene 27:6398-6406 (2008).

R. J. Youle and A. Strasser "The BCL-2 protein family: opposing activities that mediate cell death." Nat.Rev.Mol.Cell Biol. 9:47-59 (2008).

L. Zhang et al., "Role of BAX in the apoptotic response to anticancer agents." Science 290:989-992 (2000).

Z. Zhang et al., "Bax forms an oligomer via separate, yet interdependent, surfaces." J.Biol.Chem. 285:17614-17627 (2010).

106 (ZINC 14750348)

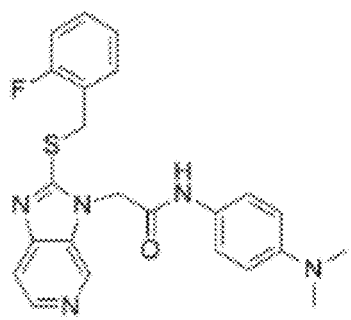
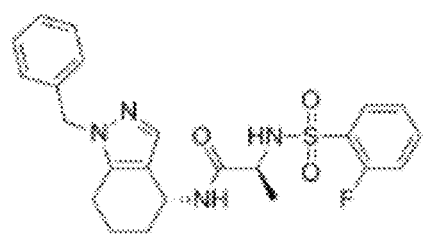
678 (ZINC08913172)
714 (ZINC24560972)
Fig. 31
Fig. 32
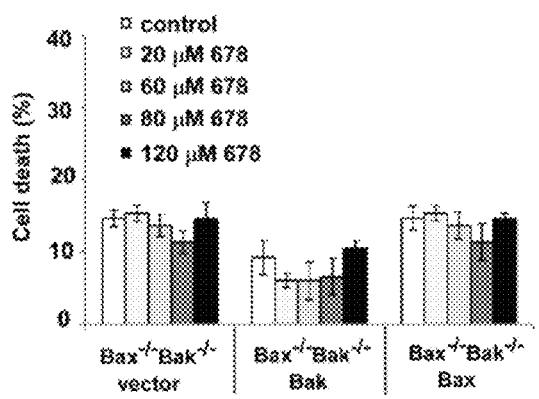
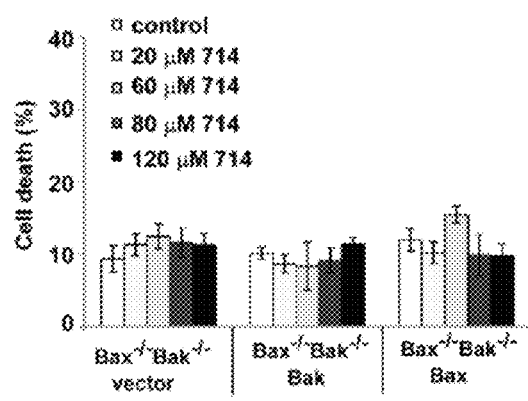
Fig. 33
Fig. 34

BAX-ACTIVATING CANCER THERAPEUTICS

RELATED APPLICATIONS

This application claims the benefit under 35 U.S.C. §119(e) of U.S. Provisional Patent Application Ser. No. 61/923,437, filed Jan. 3, 2014, having the title, "Activating the Pro-Apoptotic BCL-2 Protein BAX by Small Molecule Compounds Induces Tumor Cell Apoptosis," the disclosure of which is incorporated herein by reference in its entirety.

GOVERNMENT SUPPORT

This invention was made with government support under Grant Nos. CA106599, CA175003, RR018733, and NIH/NCRR 5P20RR018733 awarded by the National Institutes of Health. The government has certain rights in the invention.

FIELD

The subject matter of the application is in the field of biochemistry, medicine, and cancer therapeutics and it relates to activating the pro-apoptotic Bcl-2 protein Bax by administering small molecule compounds to thereby induce tumor cell apoptosis.

BACKGROUND

Resistance toward apoptosis, or programmed cell death, is a hallmark of most, perhaps all, types of human cancer. Bcl-2 proteins are the major regulators of apoptotic signaling pathways, and each Bcl-2 protein member has at least one Bcl-2 homology (BH) domain. Bcl-2 proteins can be classified into anti-apoptotic and pro-apoptotic groups. There are also two classes of pro-apoptotic Bcl-2 proteins: multiple-BH domain and BH3-only. Anti-apoptotic Bcl-2 proteins are believed to protect against disintegration of the mitochondrial outer membrane (MOM) during apoptosis, whereas pro-apoptotic Bcl-2 members promote MOM permeabilization. The expression of individual Bcl-2 protein in different types of cancer has been used as an independent prognostic marker with limited success. Recently profiling mitochondrial sensitivity to a panel of BH3 domains derived from BH3-only Bcl-2 proteins has been shown to more effectively determine the potential of different cancer cells committing apoptosis.

Neoplastic cells often show an increased ratio of anti-apoptotic to pro-apoptotic Bcl-2 proteins, which enables them to survive under adverse conditions. Thus, restoring the aberrant apoptotic pathways in tumor cells might render them more susceptible to stress conditions and subsequent apoptosis. An emerging approach for cancer therapy is to activate the apoptotic pathway directly by reducing the activity of anti-apoptotic Bcl-2 proteins or enhancing the function of pro-apoptotic Bcl-2 proteins. One strategy is to antagonize the anti-apoptotic Bcl-2 proteins. The knowledge about the structures of anti-apoptotic Bcl-2 proteins and their complexes with BH3 peptides have guided the development of small molecules and stapled peptides that indirectly activate the mitochondrial apoptotic pathway by targeting the hydrophobic groove of anti-apoptotic Bcl-2 proteins.

Another less explored approach is to identify small molecules that activate pro-apoptotic Bcl-2 proteins. The activities of the multiple-BH3 Bcl-2 proteins Bax and Bak are redundant, and it is believed that activation of either of them could induce apoptosis in almost all apoptosis paradigms examined. In the majority of cancer cells, Bax protein is functional, but its activities are largely neutralized by often overexpressed anti-apoptotic Bcl-2 proteins. Thus, activation of Bax in tumor cells could be an effective therapeutic strategy. Structural studies have demonstrated that Bax normally resides in the cytosol of healthy cells in an inactive state. The carboxyl-terminal α-helix of Bax is the membrane anchoring region, which is normally sequestered in an inhibitory hydrophobic groove of Bax, preventing its insertion into the MOM. Upon exposure to various death stimuli, through still unknown mechanisms, Bax conformation is changed, and its membrane anchoring domain is exposed and inserted in the MOM. Once translocated into mitochondria, Bax proteins are believed to oligomerize, leading to permeabilization of the MOM and subsequent release of cytochrome c from mitochondria.

In support of this model, in vitro studies using purified mitochondria or reconstituted liposomal systems with BH3 peptides or BH3-only proteins suggest that certain BH3-only proteins, particularly Bid and Bim, can bind to Bax and induce its activation. In addition, biochemical studies also demonstrate that activator BH3-only proteins can bind to the Bax canonical hydrophobic groove to induce Bax oligomerization and activation. Furthermore, crosslinking studies suggest that homo-oligomerization of Bax through an interaction between the BH3 domain and the hydrophobic binding groove (mainly α3-α5) forms "BH3-in-groove." A recent structural study reveals new detailed information about how certain BH3-only proteins can directly activate Bax, in which BH3 peptides derived from pro-apoptotic Bcl-2 proteins insert into the Bax hydrophobic groove, releasing the core domain (α1-α5) from the latch domain (α6-α8), dislodging the Bax BH3 domain, and subsequently inducing MOM permeabilization.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY

Activation of Bax by promoting its insertion into mitochondria could induce death of Bax-expressing tumor cells. In the instant disclosure, the inventors identified small molecules predicted to bind to the Bax hydrophobic groove. Among them, compound 106 is able to induce Bax-dependent tumor cell apoptosis by activating Bax and inhibiting tumor growth in vivo. The results herein indicate that it is possible to use structure-based drug design to find agents capable of activating a pro-apoptotic Bcl-2 protein by altering its conformation.

The present application provides for methods of treating cancer, anti-cancer agents, pharmaceutical compositions, and screening methods including, for example, the following embodiments:

Embodiment 1. A method of treating cancer in a human or animal patient in need thereof, said method comprising inhibiting tumor cell growth by administering to said patient an effective amount of at least one compound or a pharmaceutically-acceptable salt thereof that causes one or more effects of: (a) binding to the hydrophobic groove of Bax, (b) activating Bax, (c) promoting Bax insertion into mitochondria, (d) causing Bax-dependent mitochondrial outer membrane permeabilization, (e) inducing Bax-dependent cytochrome c release, (f) inducing cell death in Bax-expressing cells, and (g) inducing Bax-dependent apoptosis, optionally but not Bak-dependent apoptosis, in tumor cells.

Embodiment 2. The method of embodiment 1, wherein the compound is a Bax-activating compound that inhibits tumor cell growth by inducing apoptosis preferentially in tumor cells.

Embodiment 3. The method of any one of embodiments 1 or 2, wherein the compound is a Bax-activating compound that binds to the hydrophobic groove of Bax and dislocates the Bax membrane anchoring region from its binding pocket, promoting exposure of the Bax membrane anchoring region and its insertion into mitochondria.

Embodiment 4. The method of any one of embodiments 1-3, wherein the compound is selected from the group consisting of: (i) 1-{[5-(3,4-dimethylbenzyl)-1-(3-methoxybenzyl)-4,5,6,7-tetrahydro-1H-pyrazolo [4,3-c]pyridin-3-yl] carbonyl}-3-piperidinol (ZINC14750348 or compound 106); (ii) 1-{1-[(1-ethyl-3,5-dimethyl-1H-pyrazol-4-yl) methyl]-3-piperidinyl}-4-(4-methoxyphenyl)piperazine (ZINC20110124); (iii) 6-(4-(methylthio)phenyl)-2-(pyridin-3-ylmethyl)-2,3,4,6-tetrahydro-1H-benzo[4,5]imidazo[1,2-a][1,3,5]triazino[1,2-c][1,3,5]triazine (ZINC 13638227); (iv) 5-amino-N-(1-benzyl-3-piperidinyl)-2-(2-methoxyphenyl)-1-methyl-1H-benzimidazole-7-carboxamide (ZINC 12150973); (v) 5-(4-fluorophenyl)-2-[[4-(2-methoxyphenyl)piperazin-1-yl]methyl]-4-(oxolan-2-ylmethyl)-1,2,4-triazole-3-thione (ZINC 16076241); (vi) 4-(1,3-benzodioxol-5-ylacetyl)-1-isobutyl-6-(3-pyridinylmethoxy)-1,4-diazepan-2-one (ZINC 14531256); and (vii) pharmaceutically acceptable salts of any of the foregoing.

Embodiment 5. The method of any one of embodiments 1-4, further comprising administering said at least one compound with at least one other anti-cancer agent, or in conjunction with at least one other cancer therapy or treatment.

Embodiment 6. A pharmaceutical composition comprising: in an amount effective to treat a human or animal patient in need thereof, at least one compound that causes one or more effects of: (a) binding to the hydrophobic groove of Bax, (b) activating Bax, (c) promoting Bax insertion into mitochondria, (d) causing Bax-dependent mitochondrial outer membrane permeabilization, (e) inducing Bax-dependent cytochrome c release, (f) inducing cell death in Bax-expressing cells, and (g) inducing Bax-dependent apoptosis, optionally but not Bak-dependent apoptosis, in tumor cells, optionally in the form of a pharmaceutically acceptable salt of the at least one compound; optionally at least one other anti-cancer agent; and at least one pharmaceutically acceptable excipient.

These and other features, aspects, and advantages of the subject matter of this application will become better understood through reference to the following description and discussion, materials, methods, examples, appended claims, and accompanying drawings, all of which are provided by way of illustration, and are not intended to be limiting, unless otherwise specified.

BRIEF DESCRIPTION OF THE DRAWINGS

FIG. 1A shows, and FIG. 1B omits, the Bax c-terminal transmembrane α-helix in cyan.

FIG. 31 depicts the structure of compound 678.

FIG. 32 depicts the structure of compound 714.

FIG. 33 depicts cell death percent in the indicated cells 48 hours after the administration of various concentrations of compound 678.

FIG. 34 depicts cell death percent in the indicated cells 48 hours after the administration of various concentrations of compound 714.

DETAILED DESCRIPTION

Figure 1A:
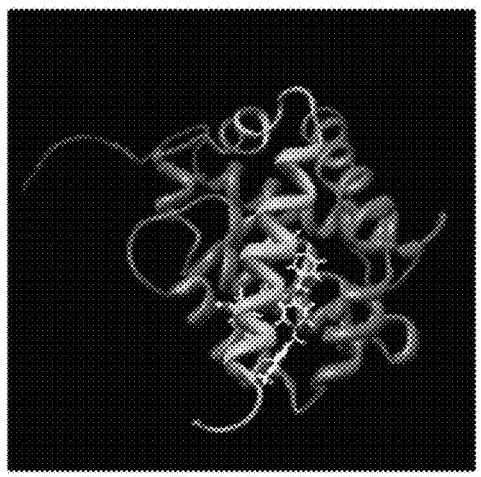
FIG. 1A-1B. These figures show the conception of a compound (white or light) binding to the hydrophobic groove of Bax (purple or dark) that, it is believed, induces Bax-dependent apoptotic cell death.

Detailed descriptions of one or more embodiments are provided herein with reference to the accompanying drawings. It is to be understood, however, that the compositions, methods, and devices according to this disclosure may be embodied in various forms. Therefore, specific details disclosed herein are not to be interpreted as limiting, but rather as a representative basis for the claims and for teaching one skilled in the art to employ the present devices, systems and methods in any appropriate manner. Accordingly, the present compositions, methods, and devices of the disclosure may be embodied in many different forms and should not be construed as being limited to the embodiments set forth herein; rather, the embodiments are provided so that this disclosure will be thorough and complete, and will fully convey the concept of the disclosure to one skilled in the art.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the measurement or number is not explicitly modified by the word about.

The terms "comprising" and "including" and "having" and "involving" and the like are used interchangeably and have the same meaning Similarly, "comprises", "includes," "has," and "involves" and the like are used interchangeably and have the same meaning Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Where ever the terms "a" or "an" are used, "one or more" is understood unless explicitly stated otherwise or such interpretation is nonsensical in context.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Although the embodiments of the present invention have been disclosed for illustrative purposes, those skilled in the art will appreciate that various modifications, additions and substitutions are possible, without departing from the scope and spirit of the invention as disclosed in the accompanying claims.

Discussion

Despite growing knowledge about the involvement of the pro-apoptotic Bcl-2 protein Bax in apoptosis, progress in translating this knowledge into the clinic has been limited. Most human cancer cells are resistant to apoptosis. Among the major regulators of apoptosis is the Bcl-2 family of proteins. An emerging cancer therapeutic strategy is directly activating the apoptotic pathways by inhibiting the activity of anti-apoptotic Bcl-2 proteins or promoting the function of pro-apoptotic Bcl-2 proteins. However, many of these strategies target the interaction among various Bcl-2 proteins, particularly the interaction between pro-apoptotic and anti-apoptotic Bcl-2 proteins. Due to functional redundancy among Bcl-2 proteins, these approaches are likely effective only on limited tumor types or display non-specific killing activities.

As an important pro-apoptotic Bcl-2 protein, Bax is involved in the development of tumors, and Bax activation has been linked to apoptosis in lung tumors. Given that Bax alone is sufficient to initiate apoptosis in almost all apoptotic paradigms, the inventors proposed that direct activation of Bax by small molecule compounds could induce death of Bax-expressing tumor cells. Accordingly, compounds that activate Bax directly may have clinical potential.

The inventors used in silico screening of a small molecule library to screen for agents likely to bind to the Bax hydrophobic groove, leading to subsequent Bax activation and Bax-dependent apoptosis. One identified compound, compound 106, exhibited strong Bax-dependent cytotoxicity either as a single agent or in combination with other chemotherapeutic drugs. Compound 106 also inhibited established tumor growth in a mouse model by inducing apoptosis in tumors. These results discussed herein provide evidence that it is possible to develop therapeutic strategies aimed at activation of Bax.

An increasing number of small molecule inhibitors have been found to target protein-protein interfaces. One example is ABT-737, a mimetic of the BH3 domain of the Bcl-2 protein BAD. ABT-737 has been shown to bind with high affinity to several anti-apoptotic Bcl-2 proteins, including Bcl-2, Bcl-$x_L$, and Bcl-w, and specifically induce the apoptotic signaling pathway. However, small molecule compounds that are able to affect the biological activities of a target protein by altering its conformation have been rarely reported. One example is the mutant p53-targeted compound PRIMA-1, whose converted forms generate adducts with thiols in mutant p53 and then induces apoptosis in tumor cells through restoration of the transcriptional transactivation function of mutant p53. Recently, an elegant study from the Walensky group has identified a small compound, BAM7, which directly binds Bax and activates Bax by triggering Bax oligomerization, thereby inducing Bax-dependent cell death. While BAM7 binds Bax at a non-canonical BH3 interaction site, compound 106, as shown in the present application, binds to the hydrophobic groove of Bax. Like BAM7, compound 106 promotes Bax insertion into the mitochondrial membrane and causes Bax-dependent cytochrome c release in vitro. In addition, compound 106 is able to inhibit tumor growth in vivo.

Even with intensive study, the mechanism of Bax activation and how Bax oligomerizes within the MOM during apoptosis is still controversial, as the detailed structural information about the activated form of full-length Bax is lacking It is generally believed that Bax exists as a monomer in the cytosol of healthy cells and functions mainly as oligomers at the MOM during apoptosis. As the Bax hydrophobic groove acts as a binding site for the BH3 domain of Bax, it may also act as a receptor for BH3-only proteins, such as tBid, Bim and Puma, to cause 'direct' activation of Bax. Cytosolic Bax contains a globular bundle of nine α helices. The last helix (α9) may regulate Bax activity, as it either anchors Bax in the MOM or resides in a hydrophobic groove on the surface of cytosolic Bax. Indeed, recent crosslinking studies have shown that the canonical hydrophobic surface groove is the interaction part of the BH3 domain for the homodimerization of Bax. Additionally, the crystal structures of Bax lacking its carboxyl terminus with the Bid BH3 peptides demonstrate the BH3 peptides can activate Bax through inserting into the hydrophobic groove of Bax.

Figure 6:
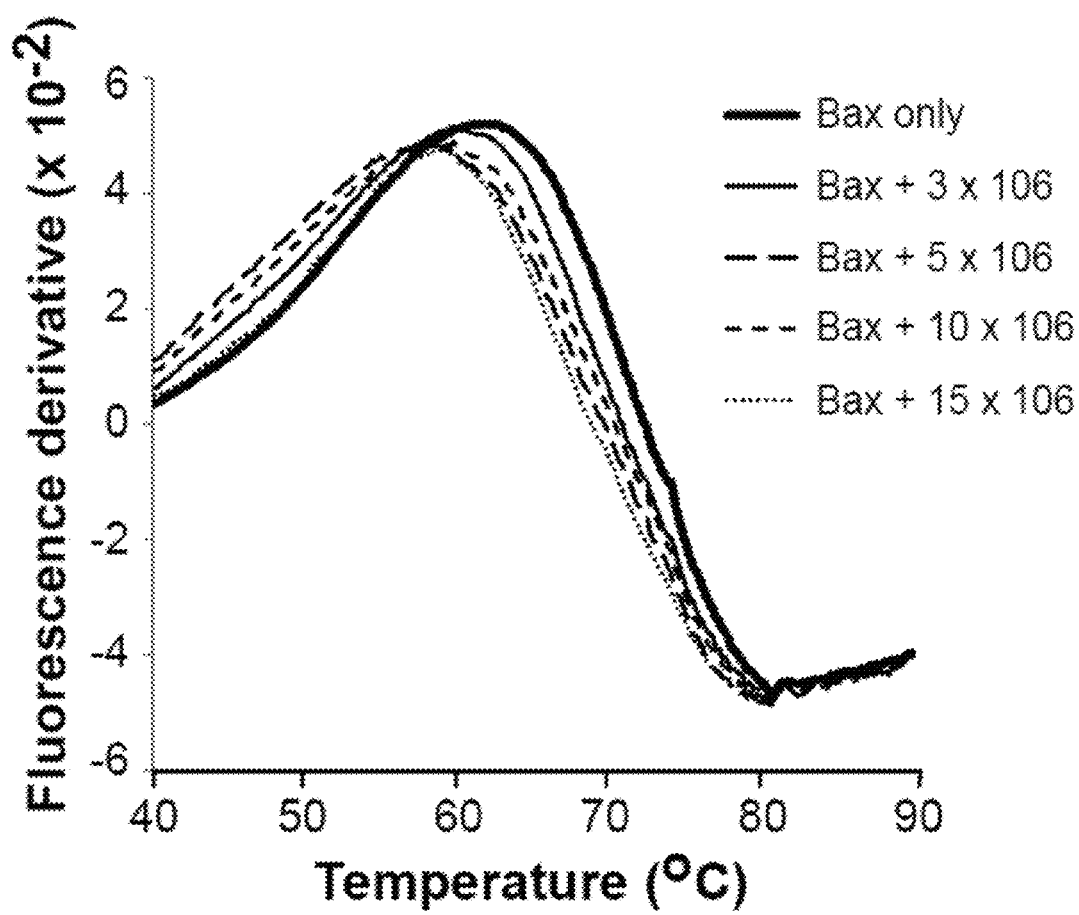
FIG. 6 depicts the effect of compound 106 on melting temperature of recombinant Bax protein, as determined by differential scanning fluorimetry. The results show compound 106 induces Bax activation in vitro.
Figure 7:
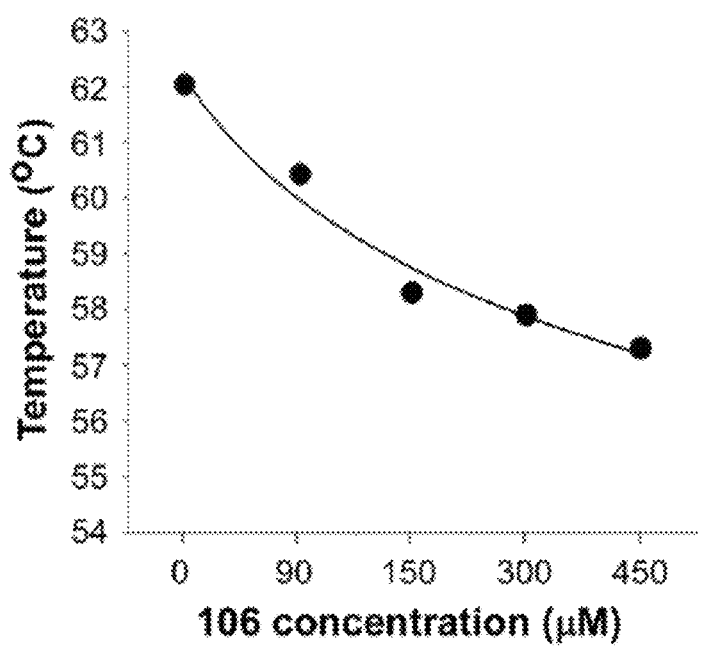
FIG. 7 depicts the melting temperature of Bax protein at increasing concentrations of compound 106.

In the present application, the inventors demonstrate by way of differential scanning fluorimetry data that compound 106 affects Bax protein stability in vitro (FIGS. 6-7). Compound 106 can also induce Bax-dependent MOM permeabilization and apoptosis (FIGS. 8-9), which provides corroborating evidence for the notion that compound 106 can alter Bax conformation and activate Bax. Based on these results, the inventors hypothesize that compound 106 binds to the Bax hydrophobic groove and dislocates the Bax membrane anchoring region from its binding pocket, leading to the exposure of the Bax membrane anchoring region and its insertion into mitochondria.

Compound 106 is preferentially toxic to transformed cells compared with their normal counterparts with similar Bax expression (FIGS. 11-17). This might be attributed to the fact that normal cells may have a sufficient pool of unoccupied anti-apoptotic proteins to tolerate anti-apoptotic blockade (for example, ABT-263) or trap activated Bax. On the contrary, tumor cells under constant external and internal death signals such as insufficient supply of nutrients, growth factors, and oxygen, are considered to be on the brink of apoptosis. Thus tumor cells may acutely respond to stressful conditions such as Bax activation because of an overwhelmed anti-apoptotic reserve.

Emerging evidence demonstrates that combinations of two or more anti-cancer drugs are able to both enhance therapeutic effects and alleviate side effects derived from high dosages of single drugs by overcoming the compensatory networks. Synergistic drug combinations can be rationalized using knowledge of single drug action mechanisms. Since promoting apoptosis in tumor cells is a promising strategy for cancer therapy, the present inventors reasoned that directly enhancing pro-apoptotic Bax activities and inhibiting anti-apoptotic Bcl-2 protein function simultaneously would achieve better therapeutic effects. Indeed, the combination of the identified Bax-activator (compound 106) and the Bcl-2 and Bcl-xL inhibitor ABT-737 functioned synergistically to induce human lung and pancreatic tumor cell apoptosis, allowing decreased doses of each drug to achieve comparable effects. Furthermore, compound 106 also shows synergy with the widely used chemotherapeutic drug carboplatin, suggesting a potentially broad application of compound 106 in cancer treatment.

Accordingly, the present application provides for methods of treating cancer, anti-cancer agents, pharmaceutical compositions, and screening methods.

In one embodiment, the disclosure provides for a method of treating cancer in a subject in need thereof, said method comprising inhibiting tumor cell growth by administering to said subject an effective amount of at least one compound or a pharmaceutically-acceptable salt thereof that causes one or more effects of binding to the hydrophobic groove of Bax, activating Bax by promoting Bax insertion into mitochondria and Bax-dependent cytochrome c release, inducing cell death in Bax-expressing cells but not Bak-expressing cells, and inducing Bax-dependent apoptosis in tumor cells. The at least one compound can comprise a Bax-activating compound that inhibits tumor cell growth by inducing apoptosis preferentially in tumor cells, in some embodiments of the present invention. In other embodiments, the at least one compound can comprise a Bax-activating compound that binds to the hydrophobic groove of Bax and dislocates the Bax membrane anchoring region from its binding pocket, promoting exposure of the Bax membrane anchoring region and its insertion into mitochondria.

In one embodiment, Bax activator compounds include compounds, such as the following compounds (as ranked by their activities to induce Bax-dependent apoptosis):

1. ZINC14750348 (Compound 106): 1-{[5-(3,4-dimethylbenzyl)-1-(3-methoxybenzyl)-4,5,6,7-tetrahydro-1H-pyrazolo[4,3-c]pyridin-3-yl]carbonyl}-3-piperidinol—(Formula: $C_{29}H_{36}N_4O_3$; Molecular Weight: 489) as shown by the following structure:

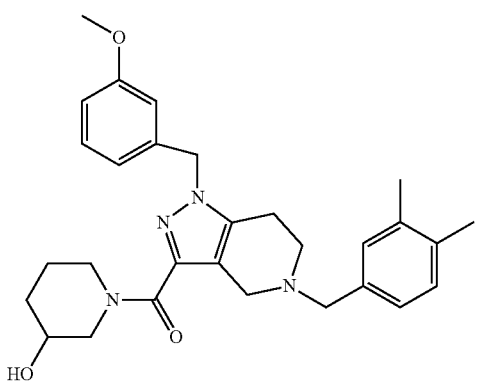 [SMILES: COc1cccc(Cn2nc(C(=O)N3CCCC(O)C3)c3c2CCN(Cc2ccc(C)c(C)c2)C3)c1]

2. ZINC20110124: 1-{1-[(1-ethyl-3,5-dimethyl-1H-pyrazol-4-yl)methyl]-3-piperidinyl}-4-(4-methoxyphenyl)piperazine—(Formula: $C_{24}H_{37}N_5O$; Molecular Weight: 412) as shown by the following structure:

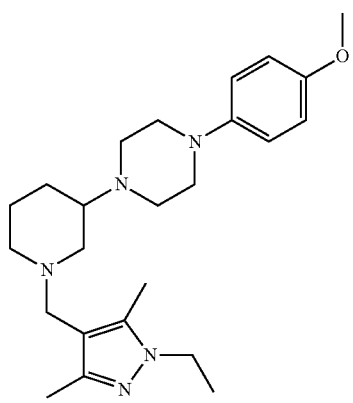 [SMILES: CCn1nc(C)c(CN2CCCC(N3CCN(c4ccc(OC)cc4)CC3)C2)c1C]

3. ZINC 13638227: 6-(4-(methylthio)phenyl)-2-(pyridin-3-ylmethyl)-2,3,4,6-tetrahydro-1H-benzo[4,5]imidazo[1,2-a][1,3,5]triazino[1,2-c][1,3,5]triazine—(Formula: $C_{24}H_{23}N_7S$; Molecular Weight: 442) as shown by the following structure:

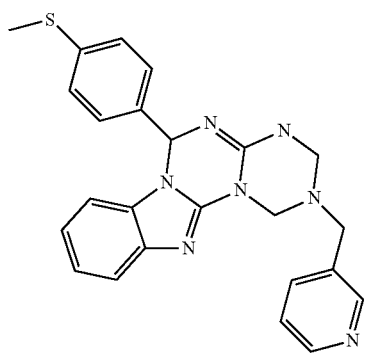 [SMILES: CSc1ccc(C2N=C3NCN(Cc4cccnc4)CN3c3nc4ccccc4n32)cc1]

4. ZINC 12150973: 5-amino-N-(1-benzyl-3-piperidinyl)-2-(2-methoxyphenyl)-1-methyl-1H-benzimidazole-7-carboxamide—(Formula: $C_{28}H_{31}N_5O_2$; Molecular Weight: 470) as shown in the following structure:

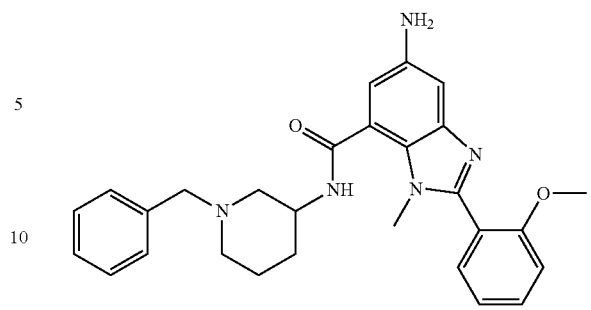

5. ZINC16076241: 5-(4-fluorophenyl)-2-[[4-(2-methoxyphenyl)piperazin-1-yl]methyl]-4-(oxolan-2-ylmethyl)-1,2,4-triazole-3-thione—(Formula: $C_{25}H_{30}FN_5O_2S$; Molecule Weight: 483.60) as shown by the following structure:

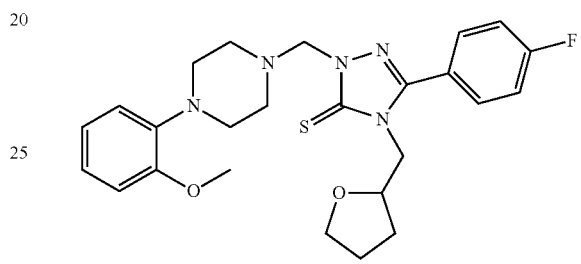

6. ZINC14531256: 4-(1,3-benzodioxol-5-ylacetyl)-1-isobutyl-6-(3-pyridinylmethoxy)-1,4-diazepan-2-one—(Formula: $C_{24}H_{29}N_3O_5$; Molecular Weight: 440) as shown by the following structure:

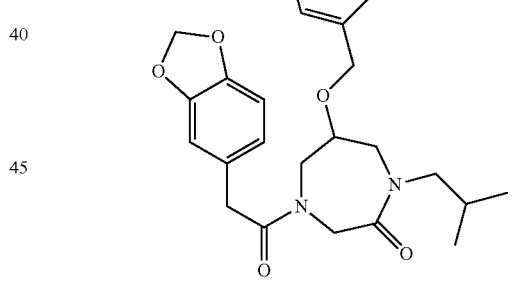

As discussed previously, in silico screening of large chemical libraries was performed and identified small molecule compounds that were predicted to bind to the Bax hydrophobic groove. For instance, compound 106 was identified and found to activate Bax, leading to Bax-dependent tumor cell apoptosis and inhibition of mouse tumor growth. As discussed, the inventors set out to examine the mechanisms by which the Bax activator inhibits tumor growth in mice. In this regard, the inventors tested the ability of the Bax activator to inhibit the growth of transplanted human tumors in mice as well as spontaneous mouse lung tumors. The inventors also investigated whether the active compound acts synergistically with other therapeutic drugs to inhibit the growth of tumors. Accordingly, the present application discloses and demonstrates how to identify small molecule compounds capable of activating the pro-apoptotic Bcl-2 protein, Bax, to induce apoptosis.

As discussed above, in one embodiment, the present application provides for pharmaceutical compositions and methods for treating cancer. "Treating" (or "treat") as used herein includes its generally accepted meaning, which encompasses prohibiting, preventing, reducing, restraining, and slowing, stopping, or reversing progression or severity of a resultant symptom. As such, the methods of this application encompass both therapeutic and prophylactic administration.

In effecting treatment of a patient afflicted with a condition, disease or disorder described herein, a compound of the present invention can be administered systemically in any form or mode, which makes the compound bioavailable in effective amounts. Systemic administration may be accomplished by administration of a compound of the present invention into the bloodstream at a site, which is separated by a measurable distance from the diseased or affected organ or tissue. For example, compounds of the present application can be administered orally, parenterally, subcutaneously, intramuscularly, intravenously, transdermally, intranasally, rectally, buccally, and the like. Oral or intravenous administration is generally preferred for treating neoplastic disease or cancer. Alternatively, the compound may be administered non-systemically by local administration of the compound of the present invention directly at the diseased or affected organ or tissue. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present application are capable of forming salts, and that the salt forms of pharmaceuticals are commonly used, often because they are more readily crystallized and purified. In all cases, the use of the pharmaceuticals described above as salts is contemplated in the description herein, and often is preferred, and the pharmaceutically acceptable salts of all of the compounds are included in the names of them.

"Pharmaceutically acceptable salt" is any suitable pharmaceutically acceptable salt and can include, but is not limited to, acid addition salts such as the hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li; alkali earth metal salts such as Mg or Ca; or organic amine salts.

According to another aspect, the present application provides a pharmaceutical composition comprising a Bax activator compound that induces cell apoptosis or a pharmaceutically acceptable salt thereof as defined hereinabove and a pharmaceutically acceptable diluent or carrier. Bax activator compounds can be synthesized utilizing known synthetic steps or purchased from various sources.

The pharmaceutical compositions of the present application are prepared by known procedures using well-known and readily available ingredients. In making the compositions, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material, which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders. Examples of suitable carriers, excipients, and diluents include lactose, dextrose, sucrose, sorbitol, mannitol, starches, gum, acacia, calcium phosphate, alginates, tragacanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. The compositions of the present application may be formulated so as to provide quick, sustained, or delayed release of the active ingredient after administration to the patient by employing procedures well known in the art.

The amount of the compound or composition of the present application which will be effective in the prevention, treatment, management, or amelioration of a proliferative disorder, such as cancer, or one or more symptoms thereof, will vary with the nature and severity of the disease or condition, and the route by which the active ingredient is administered. "Effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the progress or severity of the disease; the response of the individual patient; the particular compound administered; the mode of administration; the bioavailability characteristics of the preparation administered; the dose regimen selected; the use of concomitant medication; and other relevant circumstances.

While individual needs vary, determination of optimal ranges of effective amounts of a given cell type for a particular disease or condition is within the skill of the art. The dosage administered will be dependent upon the age, health, and weight of the recipient, kind of concurrent treatment, if any, frequency of treatment, and the nature of the effect desired.

Acceptable dosages can be extrapolated from what is known. Also, effective doses may be extrapolated from dose-response curves derived from in vitro or animal model test systems. Suitable regimens can be selected by one skilled in the art by considering such factors and by following, for example, dosages reported in the literature and recommended in the Physician's Desk Reference (57th ed., 2003). Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be empirically determined by those of skill in the art. The dosage and treatment regimen for the compounds of the instant application can be extrapolated from known clinically used anti-cancer agents. For instance, one such agent is Carboplatin, or cis-Diammine (1,1-cyclobutanedicarboxylato)platinum(II) (trade names Paraplatin and Paraplatin-AQ), which is a chemotherapy drug used against a variety of cancers, including, for example, ovarian carcinoma, lung, head and neck cancers as well as endometrial, esophageal, bladder, breast and cervical; central nervous system or germ cell tumors; osteogenic sarcoma, and as preparation for a stem cell or bone marrow transplant.

Accordingly, the dosage and treatment regimen can be determined by reading the disclosure herein and in view of the knowledge in the field. An effective amount can be any suitable amount. In some cases, an effective amount is at least about 1 µg/kg patient weight. In other cases, an effective amount is no more than about 1 g/kg. In still other cases, an effective amount ranges from about 1 µg/kg to about 100 µg/kg, from about 100 µg/kg to about 500 µg/kg, from about 500 µg/kg to about 1 mg/kg, from about 1 mg/kg to about 50 mg/kg, from about 50 mg/kg to about 100 mg/kg, from about 100 mg/kg to about 200 mg/kg, from about 200 mg/kg to about 500 mg/kg, or from about 500 mg/kg to about 1 g/kg.

In certain embodiments, the Bax activator compounds of the present application are administered in combination with other known cancer treatments and therapies, and herein refers to all pharmacological agents and/or drugs that treat cancer, and also preferably as an adjuvant therapy to avoid metastatic development.

The compositions, such as pharmaceutical compositions, of the present application can be administered by any of a number of means and routes known in the art. "Administering" means any of the standard methods of administering a compound to a subject, known to those skilled in the art. Examples include, but are not limited to parenteral, intravenous, intratumoral, intramuscular, subcutaneous, intraperitoneal, intra-articular, intracerebroventricular, or intraluminal. Also included is the "intrathecal" route, which is intended to encompass injection, infusion or instillation directly into a cavity or space surrounding an organ or body region in which an undesired immune-inflammatory response is occurring. Such spaces include the pleural space, peritoneum, subarachnoid space or dural space, or pericardial space. The generic term for administration into a sheath encasing an organ is termed "intrathecal" (see, for example, definition in Dorland's Medical Dictionary 29$^{th}$ Edition, WB Saunders (2000) and Stedman's Medical Dictionary, 27$^{th}$ Edition, Lippincott, Williams & Wilkins (2000)), as meaning "within a sheath." As used herein, this term is intended to be broader than a more commonly used definition which is limited to intracranial spaces.

Administration in vivo can be also effected in one dose, continuously or intermittently throughout the course of treatment. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient.

The compositions, methods, and products of the application are applicable to human and veterinary uses. For example, animal subjects to be treated include mammals, and more specifically humans.

The compositions, methods, and products of the application are useful for the treatment of various tumors and cancers. For instance, the cells of malignant or neoplastic tumors or cancers for treatment include: 1) carcinomas, such as those of the bladder, breast, colon, rectum, kidney, liver, lung (including small cell lung cancer), pharynx, esophagus, gall bladder, urinary tract, ovarian, cervix, uterus, pancreas, stomach, endocrine glands (including thyroid, adrenal, and pituitary), prostate, testicles and skin, including squamous cell carcinoma; 2) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma; 3) hematopoietic tumors of myeloid lineage, including acute and chronic myelogenous leukemias, myelodysplastic syndrome and promyelocytic leukemia; 4) tumors of mesenchymal origin, including fibrosarcoma and rhabdomyosarcoma; 5) tumors of the central and peripheral nervous system and meninges, including astrocytoma, neuroblastoma, glioma, schwannomas, retinoblastomas, neuroma, glioma, glioblastoma; and 6) other tumors, including melanoma, seminoma, teratocarcinoma, osteosarcoma, xenoderoma pigmentosum, keratoacanthoma, thyroid follicular cancer, anaplastic thyroid cancer and Kaposi's sarcoma. In one embodiment, the cancer is selected from the group consisting of cervical cancer, ovarian cancer, colorectal cancer, leukemia, lung cancer, thyroid cancer, CNS cancer, melanoma, renal cancer, prostate cancer, pancreatic cancer, and breast cancer.

Detailed Description of the Drawings

Further embodiments of the present disclosure can be described by reference to the accompanying drawings.

Figure 1B:
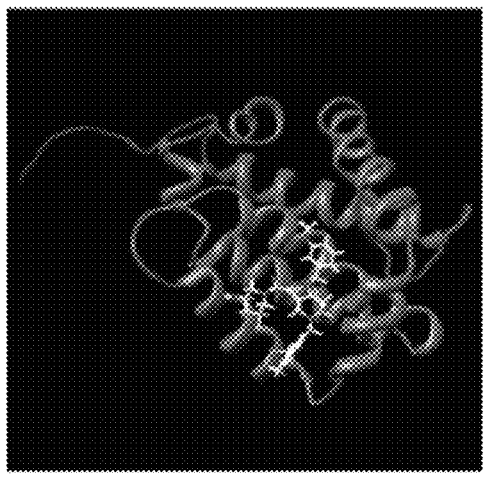
Figure 2:
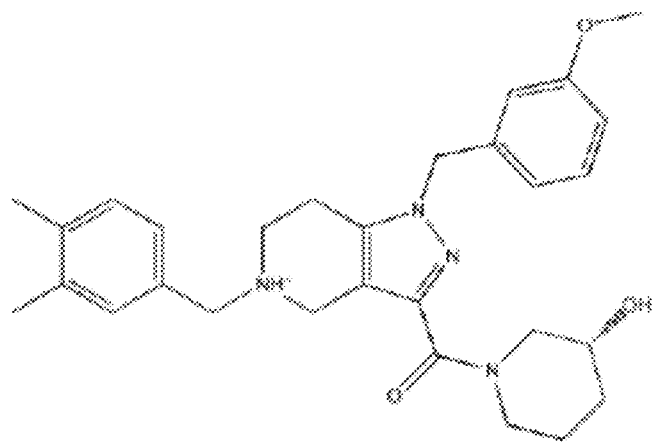
FIG. 2 depicts one embodiment of the present invention, Compound 106.
Figure 3:
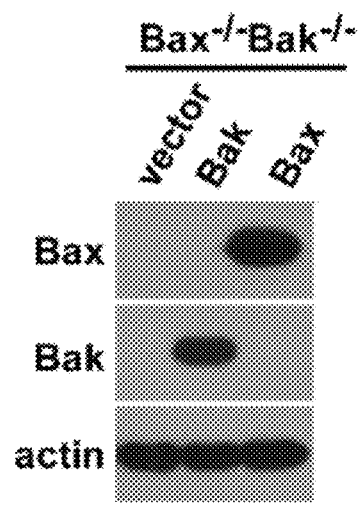
FIG. 3 depicts a western blot showing stable expression of Bax and Bak in Bak$^{-/-}$Bax$^{-/-}$ MEF cells.
Figure 4:
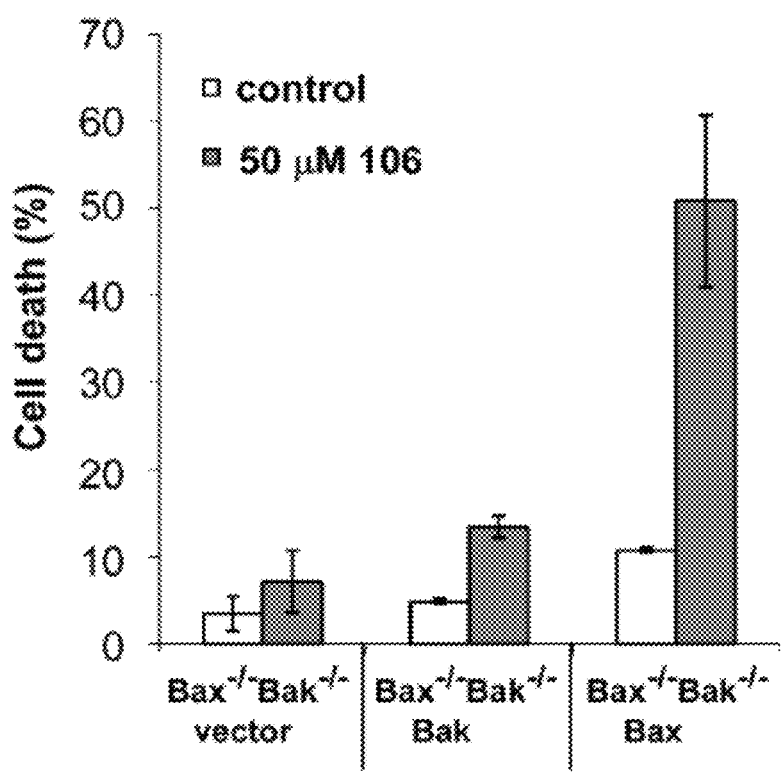
FIG. 4 shows compound 106 preferentially induced Bax-dependent cell death in Bak$^{-/-}$Bax$^{-/-}$ MEF cells stably re-expressing Bax, Bak, or the empty vector after 48 hours' treatment at 50 μM.
Figure 5:
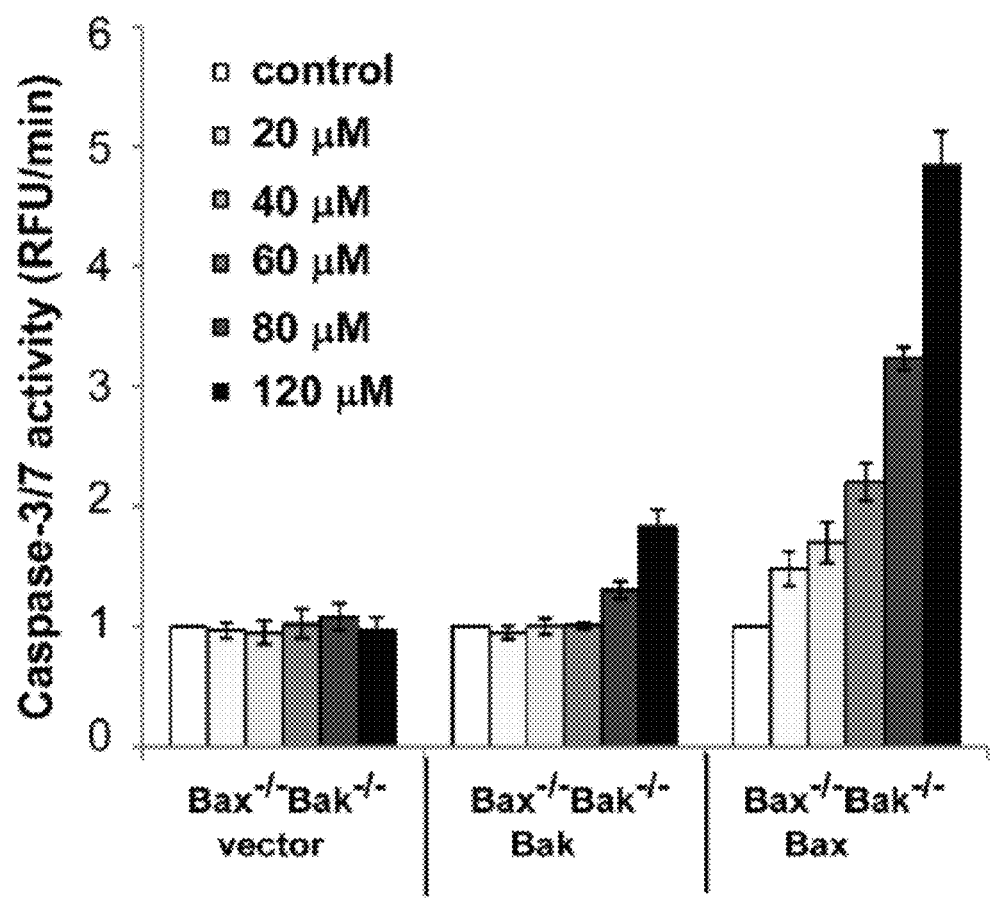
FIG. 5 plots caspase 3/7 activity versus concentration of administered compound 106 in Bak$^{-/-}$Bax$^{-/-}$ MEF cells.

FIGS. 1-5—A compound binding to the Bax hydrophobic groove induces Bax-dependent apoptotic cell death. (A) A small molecule (106) was identified by virtual screening to bind to the Bax hydrophobic groove. Here, 106 is overlaid on the Bax NMR structure with the agent (white or light) binding to the hydrophobic groove of Bax (purple or dark) in FIG. 1A. (Bax c-terminal transmembrane a-helix in cyan). The virtual screen docked complex without the Bax c-terminal transmembrane a-helix appears in FIG. 1B. (B) FIG. 2 shows the structure of compound 106. (C) Stable expression of Bax and Bak in Bak$^{-/-}$Bax$^{-/-}$ MEF cells was examined by western blot, shown in FIG. 3. (D) Compound 106 preferentially induced Bax-dependent cell death, as shown in FIG. 4. The indicated MEF cells were treated with compound 106 for 48 hours, and cell viability was measured by propidium iodide exclusion. (E) FIG. 5 shows that Compound 106 activated caspase 3/7 only in Bax-expressing cells. Caspase 3/7 activity was measured 24 hours after the treatment of compound 106 using a luminescent assay. The values are normalized to those obtained in the untreated cells. All the data of caspase 3/7 activity and cell death are shown as mean±standard deviation of triplicate experiments. Experiments are representative of three independent experiments.

Figure 8:
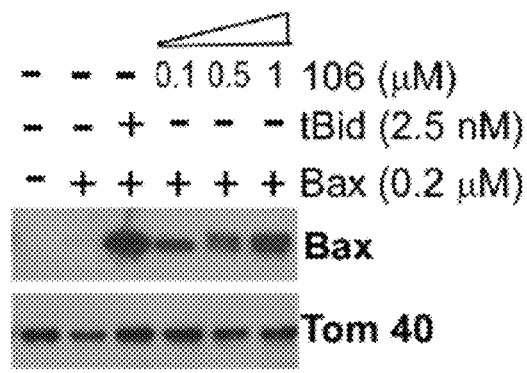
FIG. 8 depicts western blot analysis of Bax levels inserted in mitochondria following incubation with Bax, tBid, and compound 106.
Figure 9:
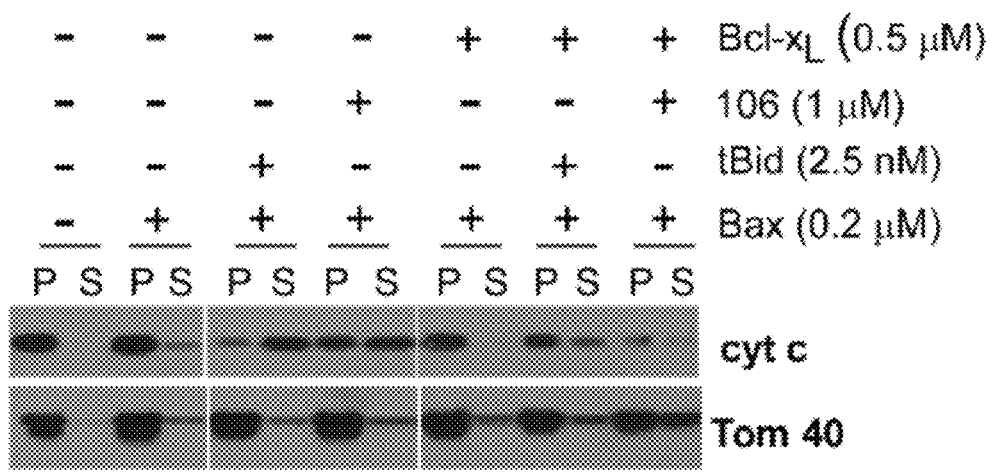
FIG. 9 depicts the effects of compound 106 on Bax-dependent cytochrome c release following incubation of mitochondria with the indicated reagents. The results demonstrate that compound 106 caused Bax-dependent mitochondrial outer membrane permeabilization.
Figure 10:
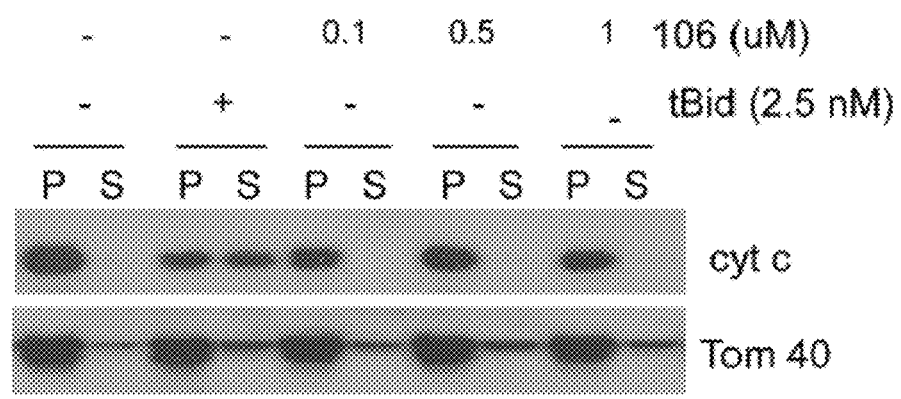
FIG. 10 depicts the same experiment as in FIG. 9, but targeting Bak-dependent behavior. Compound 106 does not induce Bak-dependent mitochondrial outer membrane permeabilization.

FIGS. 6-10—Compound 106 induces Bax activation in vitro. (A) In FIG. 6, recombinant Bax protein (30 µM) was incubated with various doses of compound 106 (90-450 µM). Melting temperature (Tm) of Bax protein was determined by differential scanning fluorimetry. (B) In FIG. 7, Tm of Bax protein decreased as the concentration of compound 106 increased. (C) Compound 106 induced Bax insertion into mitochondria. Mitochondria purified from Bak$^{-/-}$Bax$^{-/-}$MEF cells were incubated with Bax, tBid, and compound 106. Bax levels inserted in mitochondria were determined by western blot, shown in FIG. 8. (D) Compound 106 caused Bax-dependent mitochondrial outer membrane permeabilization. Mitochondria isolated from Bak$^{-/-}$Bax$^{-/-}$ MEF cells were incubated with the indicated reagents, and the effects of compound 106 on Bax-dependent cytochrome c release were determined and appear in FIG. 9. (E) Compound 106 cannot induce Bak-dependent mitochondrial outer membrane permeabilization, as shown in FIG. 10.

Figure 11:
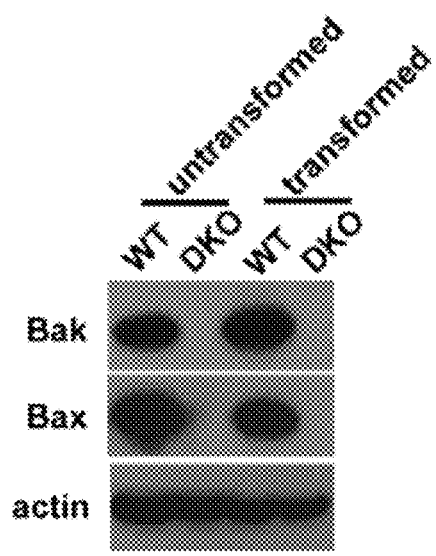
FIG. 11 depicts Bax and Bak expression in wild type and DKO, untransformed and transformed, MEF cell lines examined by western blot.
Figure 12:
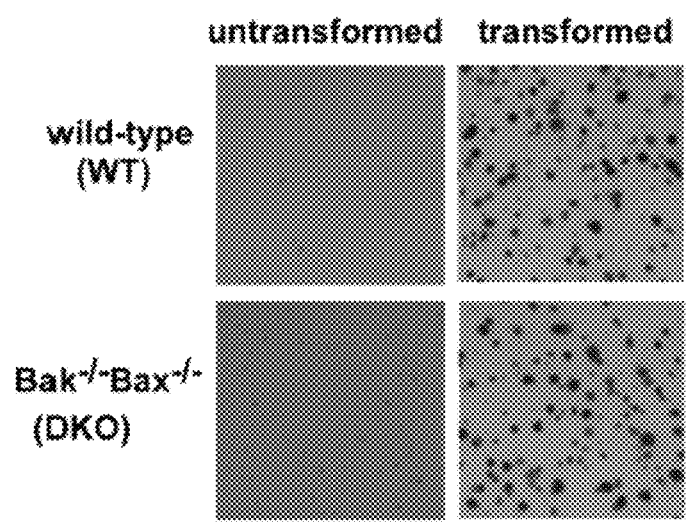
FIG. 12 provides images at 10-fold magnification of indicated MEF cells cultured in soft agar.
Figure 13:
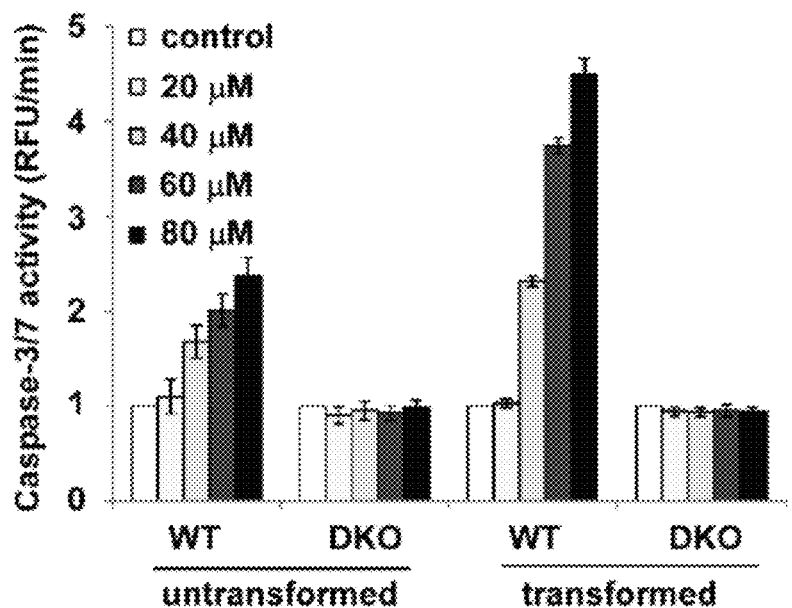
FIG. 13 reports caspase 3/7 activity versus various concentrations of compound 106 in the indicated MEF cells after 24 hours.
Figure 14:
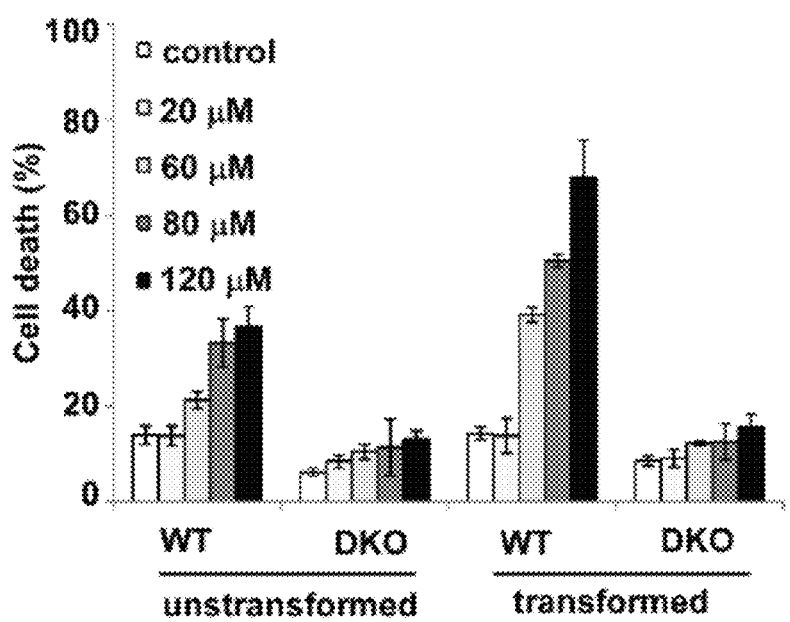
FIG. 14 depicts cell death percent versus concentration of compound 106 after 48 hours.
Figure 15:
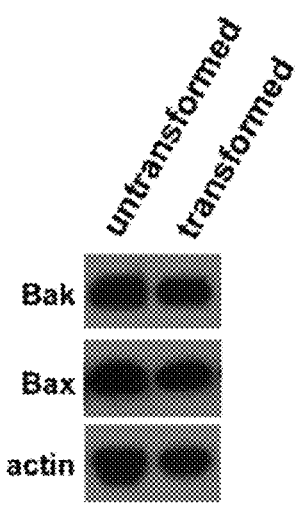
FIG. 15 depicts western blot analysis of Bax expression in untransformed and transformed NHBE cells.
Figure 16:
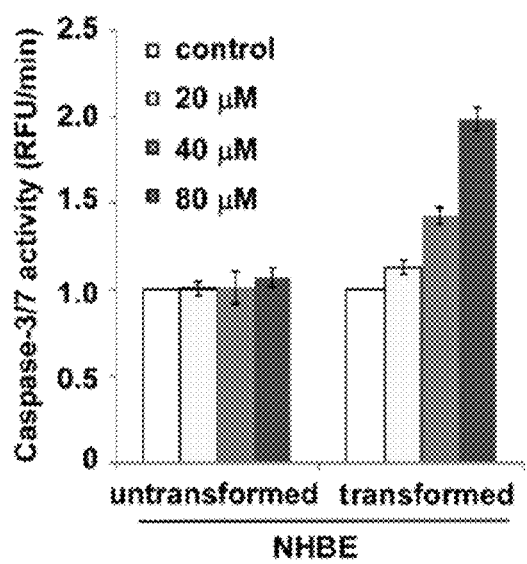
FIG. 16 plots caspase 3/7 activity versus various concentrations of compound 106 in the indicated NHBE cells after 24 hours.
Figure 17:
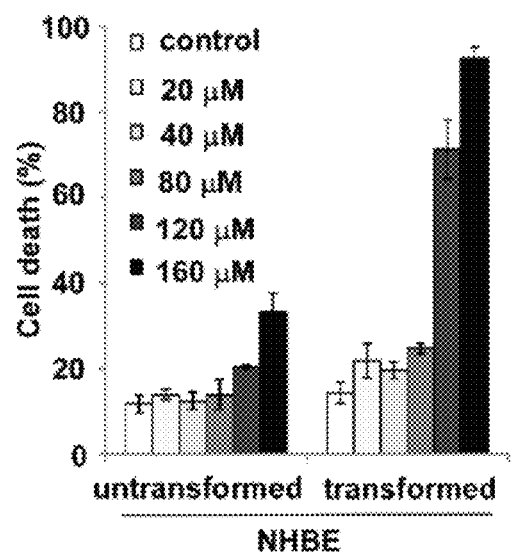
FIG. 17 depicts cell death percent versus concentration of compound 106 after 24 hours in the indicated NHBE cells.

FIGS. 11-17—Compound 106 preferentially induces apoptotic cell death in transformed cells. (A) In FIG. 11, Bax and Bak expression in the indicated MEF cell lines was examined by western blot. (B) The indicated cells were cultured in soft agar and representative images are shown in FIG. 12. The bright field images were taken using a Nikon TS100 microscope with a Nikon DSL1 digital camera at 10× magnification. (C) Compound 106 induced caspase 3/7 activation preferentially in transformed wild-type cells. The indicated MEF cells were incubated with various concentrations of compound 106 for 24 hours and caspase 3/7 activity was measured, as shown in FIG. 13. (D) The viability of the indicated MEF cells was determined 48 hours following compound 106 treatment. More cell death was detected in transformed wild-type cells, as shown in FIG. 14. (E) Bax expression in untransformed and transformed NHBE cells were detected by western blot, as shown in FIG. 15. (F) Compound 106 induced more caspase 3/7 activation in transformed NHBE cells than untransformed NHBE after the treatment of compound 106 for 24 hours, as seen in FIG. 16. (G) The effects of compound 106 on the viability of the indicated NHBE cells were examined following 24 hour incubation. More cell death was detected in transformed NHBE cells, as shown by FIG. 17. All the data of caspase3/7 activity and cell death are shown as mean±standard deviation of triplicate experiments. Experiments are representatives of three independent experiments.

Figure 18:
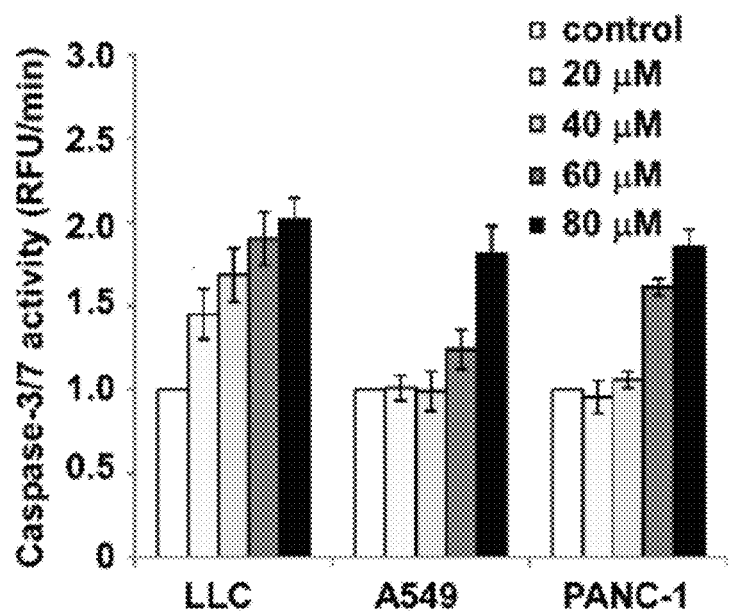
FIG. 18 depicts caspase 3/7 activity in indicated mouse and human tumor cell lines at 24 hours after administration of compound 106 at varying concentrations.
Figure 19:
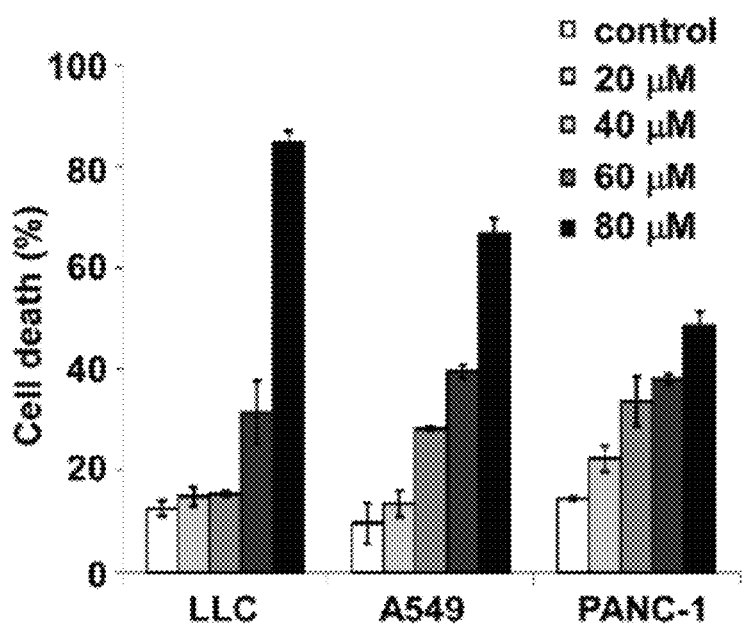
FIG. 19 depicts cell death percent at 48 hours following administration of compound 106 in the indicated cell lines.
Figure 20:
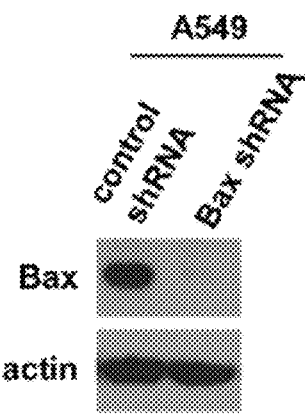
FIG. 20 depicts western blot analysis of Bax expression in A549 cells. A549 cells having reduced Bax expression due to a small hairpin RNA (shRNA) were compared to control A549 cells expressing a control shRNA vector.
Figure 21:
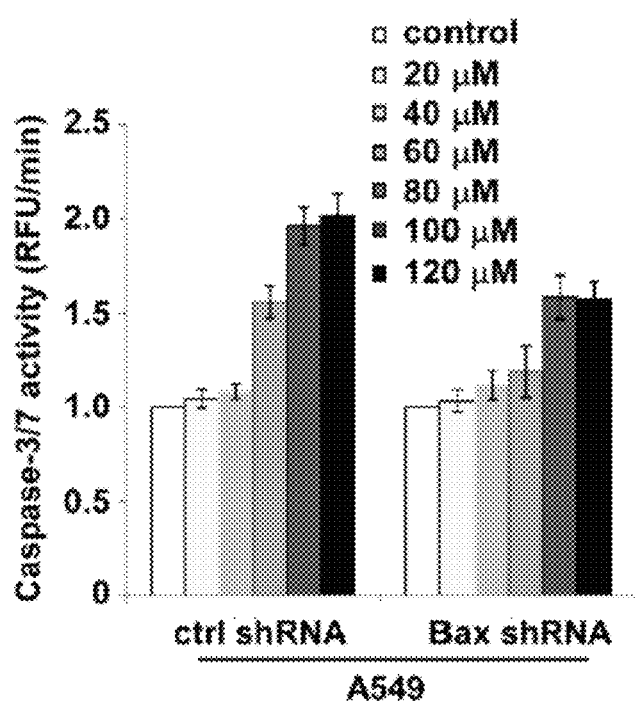
FIG. 21 depicts caspase 3/7 activity after 24 hours versus various concentrations of compound 106 administered to the indicated A549 cells.
Figure 22:
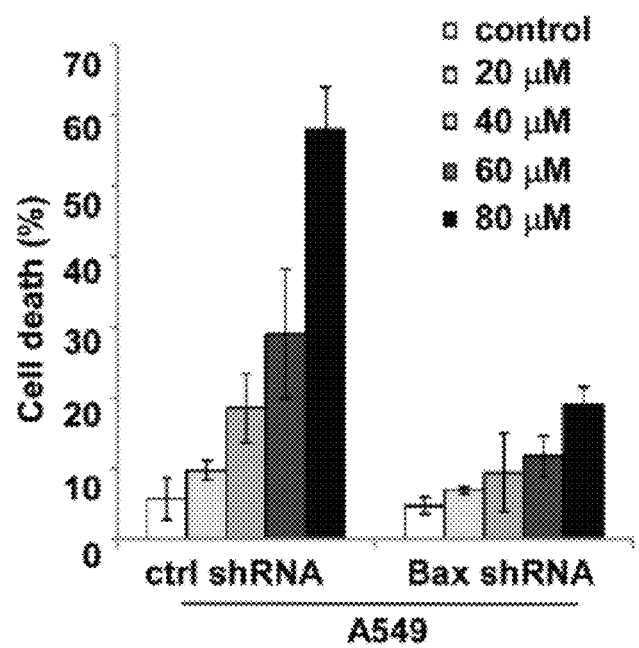
FIG. 22 depicts cell death percent 48 hours after administration of compound 106 in indicated A549 cells.
Figure 23:
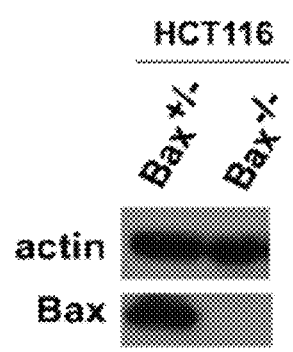
FIG. 23 depicts western blot analysis of actin and Bax in Bax$^{+/-}$ and Bax$^{-/-}$ HCT116 cells.
Figure 24:
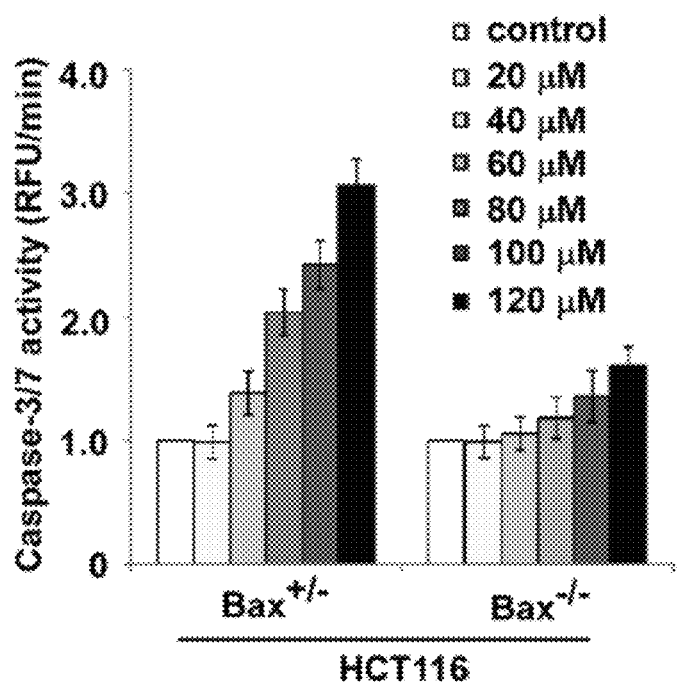
FIG. 24 depicts caspase 3/7 activity in the indicated HCT116 cells twenty-four hours after administration of various concentrations of compound 106.
Figure 25:
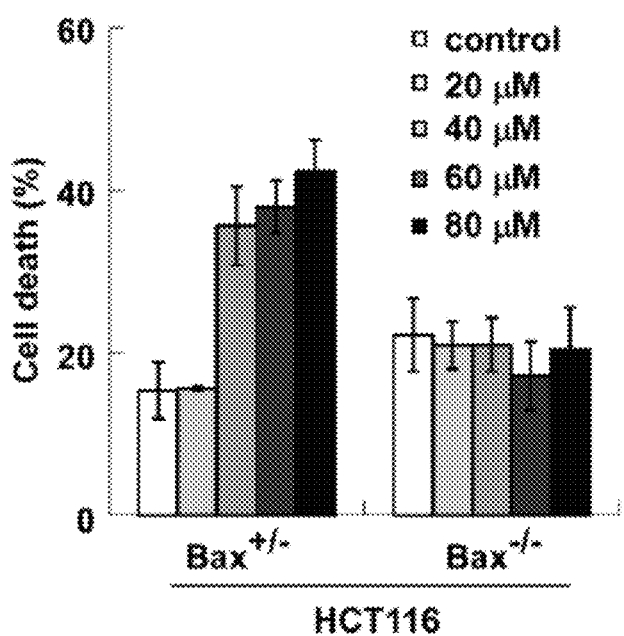
FIG. 25 depicts cell death percent in the indicated HCT 116 cells forty-eight hours after administering various concentrations of compound 106.

FIGS. 18-25—Compound 106 induces apoptotic cell death in human tumor cells death in a Bax-dependent fashion. (A) Upon treatment with compound 106 for 24 hours, caspase 3/7 activity of mouse Lewis lung carcinoma (LLC) and human tumor cell lines A549 and PANC-1 was determined. See FIG. 18. (B) Tumor cells were killed by compound 106 in a dose-dependent fashion, as seen in FIG. 19. LLC, A549, and Panc-1cells were treated with the indicated concentrations of compound 106 for 48 hours, and cell viability was measured. (C) Bax expression in A549 cells was reduced by a small hairpin RNA (shRNA). The expression levels of Bax were determined by western blot, as shown in FIG. 20. (D) Compound 106 induced higher caspase 3/7 activation in A549 cells with normal levels of Bax expression following 24 hour treatment, as seen in FIG. 21. (E) Less cell death was detected in A549 cells with reduced Bax expression than their counterparts expressing a control shRNA vector after 48 hour incubation with compound 106, as shown in FIG. 22. (F) Bax expression in the indicated colorectal carcinoma HCT116 cells was determined by western blot. See FIG. 23. (G) Caspase 3/7 activity in the indicated HCT116 cells was measured 24 hours after compound 106 treatment and shown in FIG. 24. (H) Compound 106 preferentially induced cell death in Bax expressing HCT116 cells after 48 hour incubation, as seen in FIG. 25. All caspase 3/7 measurement and cell death data represent mean±standard deviation of triplicate experiments. Experiments are representative of three independent experiments.

FIGS. 26A-26D—Compound 106 functions synergistically with carboplatin or ABT-737 to induce human tumor cell death. (A) Upon 48 hour-treatment with various combinations of compound 106 (80-240 µM) and carboplatin (80-240 µM) at a constant concentration ratio, the percentage of A549 cell death was measured. The values combination index (CI) and fractional activity (Fa) were calculated as described in Materials and Methods, and shown in FIG. 26A. (B) PANC-1 cells were treated with various doses of compound 106 (3.3-240 µM) and carboplatin (3.3-240 µM) at a constant dose ratio for 48 hours and cell death was measured. The values of CI were determined and shown in FIG. 26B. (C) A549 cells were treated with various combinations of compound 106 (2.4-196 µM) and ABT-737 (0.84-70 µM) at a fixed concentration ratio for 48 hours and cell death was measured. The values of combination index (CI) were determined and shown in FIG. 26C. (D) Upon 48 hour-treatment with various concentrations of compound 106 (3.4-140 µM) and ABT-737 (0.84-35 µM) at a fixed dose ratio, the percentage of PANC-1 cell death was determined and CI values were computed and shown in FIG. 26D. All Experiments were performed independently three times.

Figure 27:
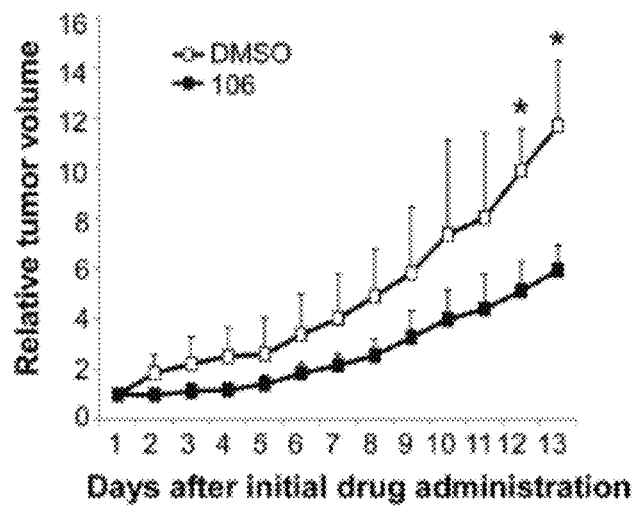
FIG. 27 plots in vivo relative tumor volume versus days after initial drug administration of LLC tumor cells in female C57BL6 mice treated daily with intraperitoneal injections of compound 106 or DMSO.
Figure 28:
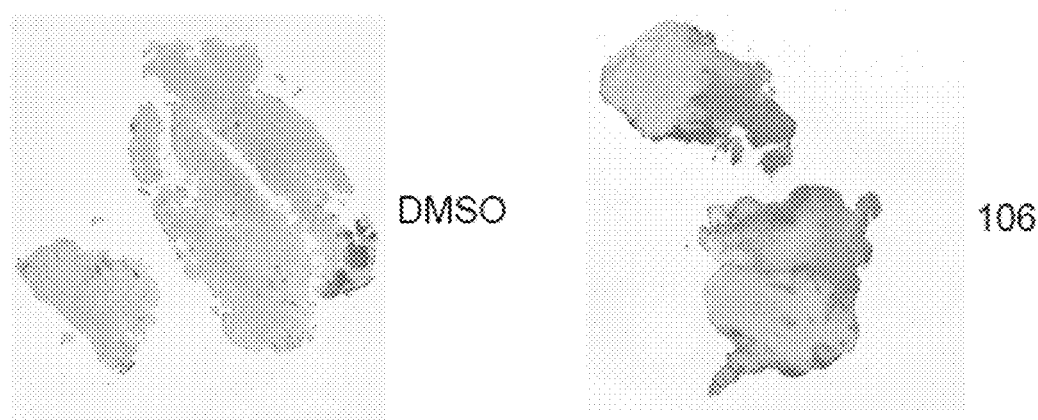
FIG. 28 depicts photomicroscopy images at 20-fold magnification of tumor sections from the mice tested in FIG. 27 showing apoptotic cells detected by TUNEL assay.
Figure 29:
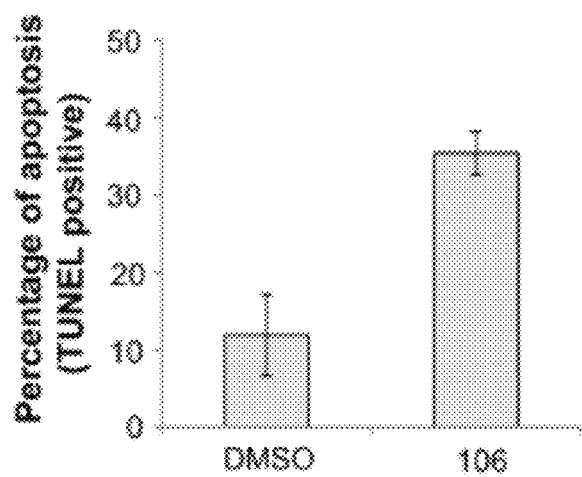
FIG. 29 plots the percentage of apoptotic cells in tumors treated in vivo with either DMSO or compound 106.
Figure 30A:
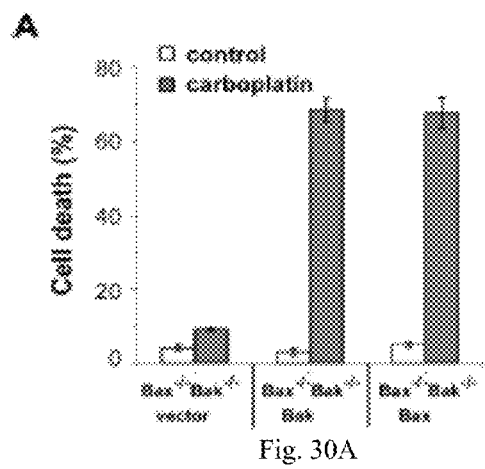
FIGS. 30A-30E plot cell death percentage of $Bak^{-/-}$ $Bax^{-/-}$ MEF cells stably re-expressing of Bax, Bak, or the empty vector treated with 50 μM carboplatin (FIG. 30A), 1 μM doxorubicin (FIG. 30B), 0.2 μg/ml Actinomycin D (FIG. 30C), 5 μM etoposide (FIG. 30D), or 40 μg/ml vincristine (FIG. 30E) respectively.
Figure 30B:
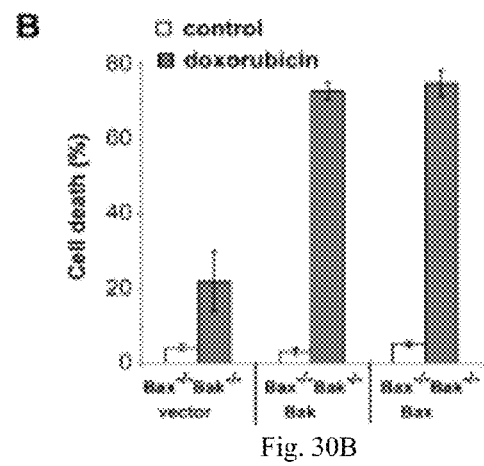
Figure 30C:
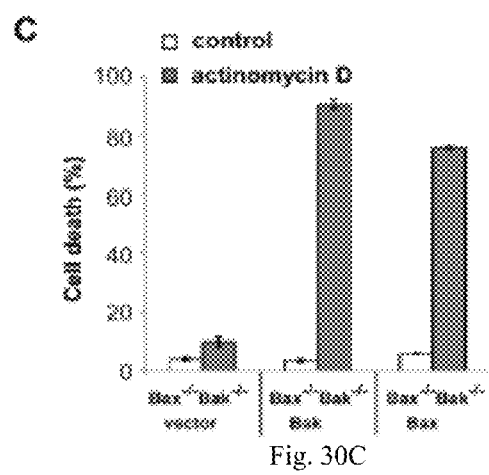
Figure 30D:
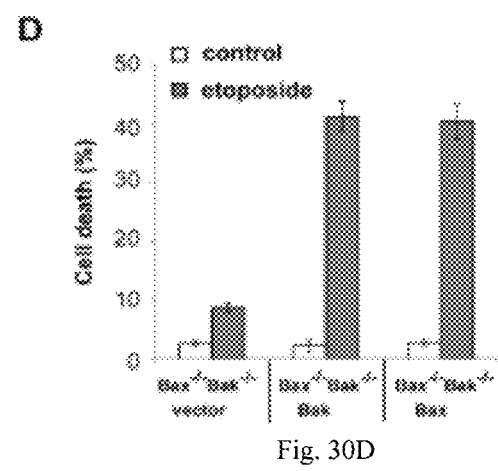
Figure 30E:
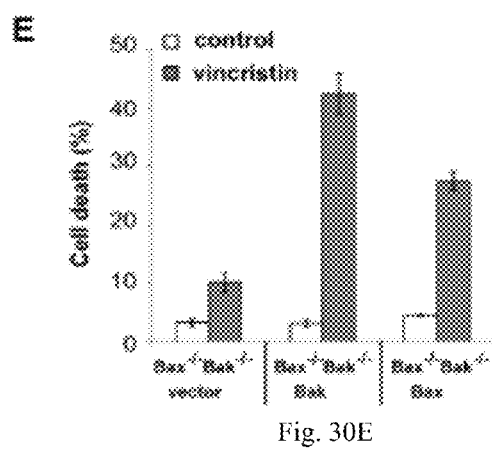

FIGS. 27-29—Compound 106 inhibits mouse lung tumor growth and induces apoptosis of tumor cells in vivo. (A) Female C57BL6 mice were inoculated subcutaneously (s.c.) with $1\times10^6$ LLC tumor cells on the right flank. Daily intraperitoneal injection of compound 106 at 40 mg/kg/day was initiated when the tumor size reached 200 mm³ and continued through the end of the experiment. Tumors were measured every day. Data are shown in FIG. 27 as mean±standard deviation of tumor volume of 5 animals in either vehicle control or compound 106-treated group. Asterisks indicate P<0.05, Student's unpaired t test. (B) Apoptotic cells in tumor sections were detected by TUNEL (Terminal deoxynucleotidyl Transferase Bioten-dUTP Nick End Labeling) assay. Representative images of the indicated tumor sections are shown in FIG. 28. The bright field images of tumor sections were acquired using a ScanScope CS digital slide scanner (Aperio; Vista, Calif.) with 20-fold magnification. (C) The percentage of apoptotic cells in tumors of 106-treated mice is higher than that of DMSO-treated mice, as seen in FIG. 29. Data are mean±standard deviation of three independent tumor sections.

FIGS. 30A-30E—Chemotherapeutic drugs displayed similar cytotoxic activities on cells re-expressing Bax or Bak. Bak⁻/⁻Bax⁻/⁻ MEF cells stably re-expressing of Bax, Bak, or the empty vector were treated with 50 µM carboplatin (FIG. 30A), 1 µM doxorubicin (FIG. 30B), 0.2 µg/ml Actinomycin D (FIG. 30C), 5 µM etoposide (FIG. 30D), or 40 µg/ml vincristine (FIG. 30E) respectively. The percentage of cell death was determined 48 hours later. The data depict mean±standard deviation of triplicate experiments. Experiments are representative of three independent experiments.

Figure 35:
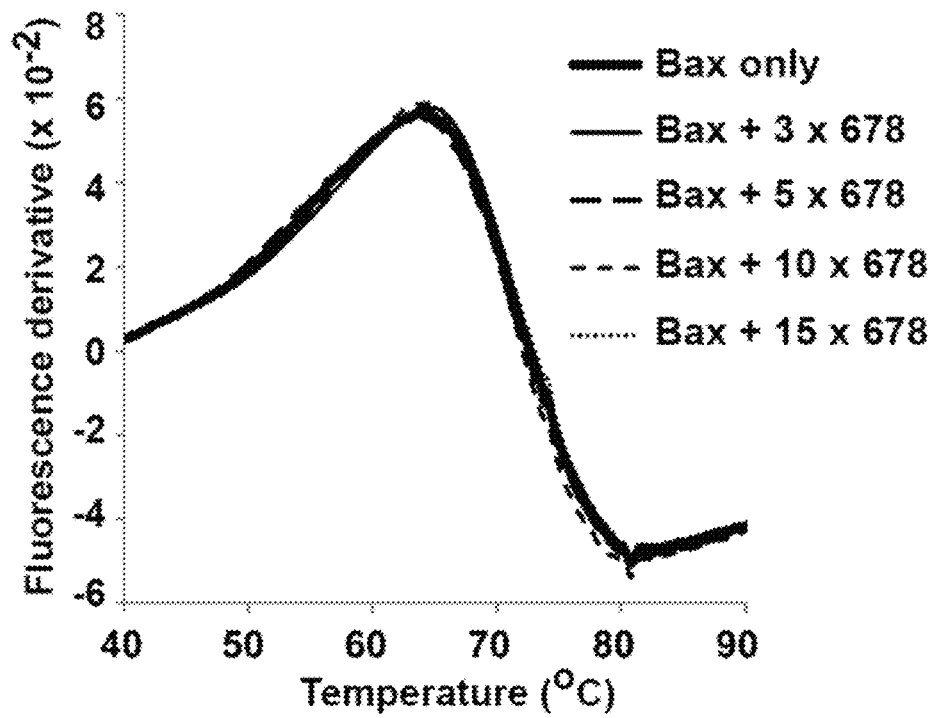
FIG. 35 depicts the effect of compound 678 on melting temperature of recombinant Bax protein, as determined by differential scanning fluorimetry.
Figure 36:
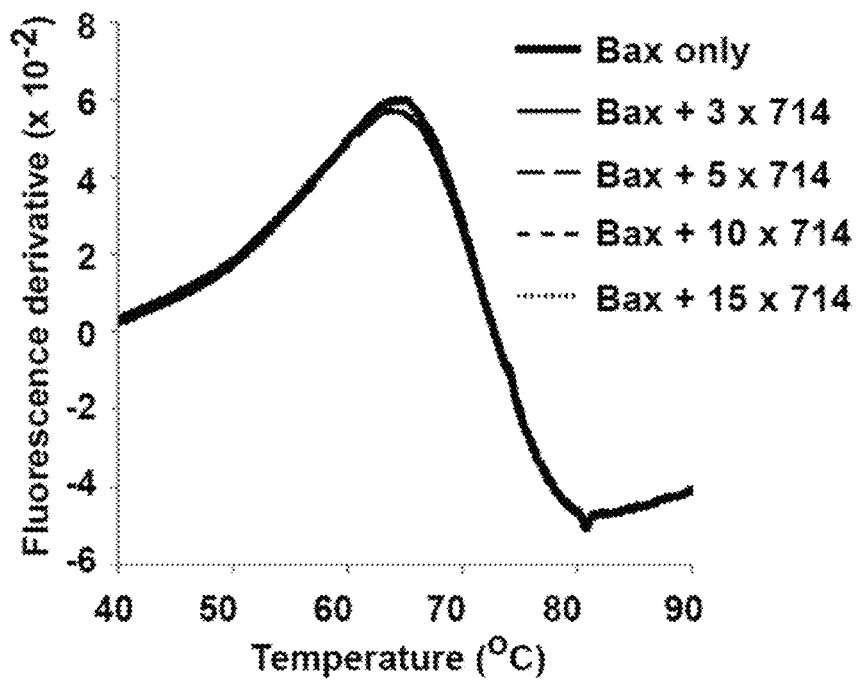
FIG. 36 depicts the effect of compound 714 on melting temperature of recombinant Bax protein, as determined by differential scanning fluorimetry.

FIGS. 31-36—Non-toxic molecules failed to affect Bax protein conformation. (A) Schematic illustration of the structures of compound 678 (FIG. 31) and compound 714 (FIG. 32). (B) Compound 678, having results shown in FIG. 33, or compound 714, having results shown in FIG. 34, did not induce cell death in the indicated cell lines after 48 hour treatment. The data shown are mean±standard deviation of triplicate experiments. Experiments are representatives of three independent experiments. (C) 30 µM of Bax protein was incubated with various doses of compound 678 (90-450 µM) or compound 714 (90-450 µM). Melting temperature (Tm) of Bax protein was determined by differential scanning fluorimetry. Both compound 678 and compound 714 failed to alter Tm of Bax protein, as seen in FIG. 35 (for compound 678) and FIG. 36 (for compound 714).

Figure 37A:
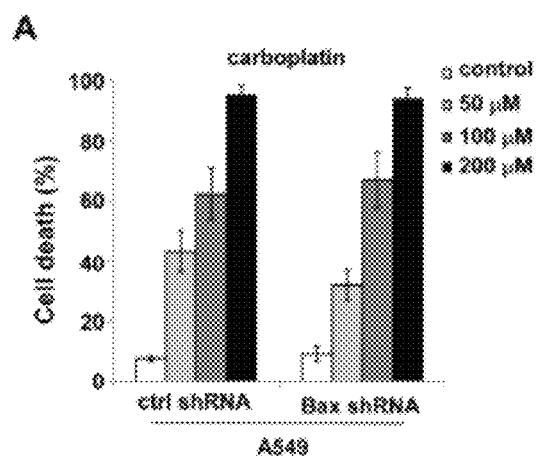
FIGS. 37A-37B plot cell death percent versus various concentrations of carboplatin (FIG. 37A) and vincristine (FIG. 37B) 48 hours after administration, in the indicated A549 cells.
Figure 37B:
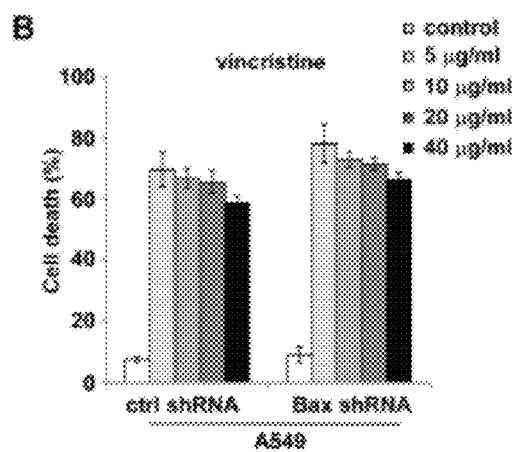
Figure 37C:
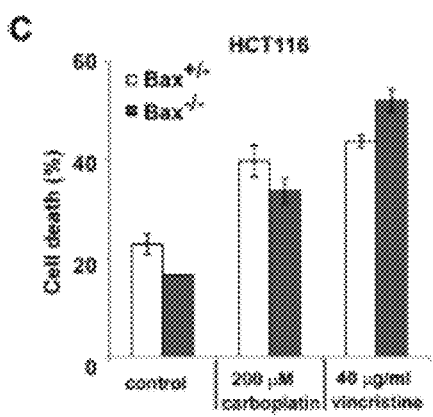
FIG. 37C plots cell death percent 48 hours after administration of carboplatin or vincristine in HCT116 cells that have and lack Bax expression.

FIG. 37A-37C—Deficiency in Bax expression did not affect cell sensitivity to some chemotherapeutic drugs. Decrease in Bax expression did not affect killing activities of carboplatin (FIG. 37A) and vincristine (FIG. 37B) in A549 cells following 48 hour incubation. (C) Lack of Bax expression in HCT116 cells did not affect killing activities of carboplatin and vincristine after 48 hour treatment, as seen in FIG. 37C. All the data represent mean±standard deviation of triplicate experiments. Experiments are representative of three independent experiments.

Materials and Methods

The following methods and materials are used in various experiments described herein as well as in carrying out certain embodiments of the invention.

Reagents: Compound 106, [5-[(3,4-dimethylphenyl)methyl]-1-[(3-methoxyphenyl)methyl]-4,5,6,7-tetrahydropyrazolo[4,3-c]pyridin-5-ium-3-yl]-[(3R)-3-hydroxypiperidin-1-yl]methanone, (ZINC# 14750348) was obtained from Chembridge (San Diego, Calif.). ABT-737 was provided by Abbott Laboratories (Abbott Park, Ill.). Carboplatin and vincristine were purchased from Enzo (Farmingdale, N.Y.). Propidium iodide was obtained from Molecular Probes (Eugene, Oreg.). Dulbecco's Modified Eagle's Medium (DMEM) and penicillin/streptomycin were obtained from Mediatech (Manassas, Va.), and fetal bovine serum was purchased from Gemini (Broderick, Calif.). Antibodies were anti-actin mAb (Sigma, St. Louis, Mo.), anti-Bax pAb (Santa Cruz, Santa Cruz, Calif.), anti-cytochrome c mAb (Becton Dickinson, Franklin Lakes, N.J.), anti-Bak, NT pAb (Millipore, Billerica, Mass.) and anti-Tom40 pAb (Santa Cruz). Recombinant Bcl-2 proteins (hBcl-$x_L$, htBid and hBax) were acquired as described previously.

Cell lines: Bak$^{-/-}$Bax$^{-/-}$ murine embryonic fibroblast (MEF) cells expressing the empty vector, Bak or Bax were cultured as described previously. Human non-small cell lung carcinoma A549 and human pancreatic carcinoma Panc-1 were purchased from ATCC (Manassas, Va.). Untransformed and transformed MEF cells were kindly provided by Dr. Wei-Xing Zong. Bax$^{+/-}$ and Bax$^{-/-}$ HCT116 cells were obtained from Drs. Bert Vogelstein and Kenneth Kinzler. All cells were cultured at 37° C. in a 5% $CO_2$ incubator as described previously (42). To generate A549 cells with reduced Bax expression or vector control, cells were first infected by Bax shRNA lentiviral particles or control shRNA lentiviral particles (Santa Cruz). Stable cells were obtained by culturing cells in the medium with 10 µg/ml puromycin.

Virtual screen: The NMR structure of Bax (PDB entry 1F16) was used for the target of the virtual screen. The goal of the virtual screen was to find a small molecule that bound Bax in the carboxyl-terminal transmembrane helix binding site and blocked the carboxyl-terminal transmembrane helix from binding. 10,967,615 potential small molecules in ZINC drug-like database were screened for binding to the carboxyl-terminal transmembrane helix binding site pocket in the Bax hydrophobic groove. Surflex v2.6 was used for the virtual screening with the pgeom option (-spindense 6.0+ premin+remin-multistart 4-div_rms 0.5-ndock_final 20). The protomol was generated using the residues essential for the interaction with the Bax carboxyl-terminal transmembrane region. The carboxyl-terminal transmembrane residues 174-89 were used to identify binding pocket residues within 5 angstroms resulting in residues 91, 94-96, 98-9, 108-9, 111-3, 115-9 being used for protomol generation with proto_thresh and proto_bloat values of 0.18 and 0, respectively (the Bax carboxyl-terminal transmembrane region was removed prior to the protomol generation). Compounds docking correctly in the Bax hydrophobic groove were ranked and the top 100 compounds with the highest scores were identified and purchased to examine their biological activities. Virtual screening experiments were carried out at the Molecular Modeling Facility of the James Graham Brown Cancer Center and the University of Louisville Cardinal Research Cluster.

Differential scanning fluorimetry: Fluorescence melting curves were obtained using StepOne™ Plus Real-Time PCR Thermocycler (ABI, Grand Island, N.Y.). Reaction volume was 20 µL with a melting profile obtained from 20° C. to 99° C. at 0.5° C./minute with an initial hold time of 10 minutes. Sypro Orange (Molecular Probes) was used as the fluorescent dye at 5× concentration. The final concentration of BAX protein was 25 µM with concentrations of ligand at 75, 125, 250 and 375 µM in 20 mM HEPES, 20% glycerol, pH 7.5 and a fixed final concentration of 2.25% DMSO (v/v). Samples were run in triplicate with appropriate controls. Raw data were exported to Origin 7.0 (OriginLab Corporation, Northampton, Mass.) for subsequent data analysis. Tm values were obtained from the temperature maximum of the first derivative of the raw fluorescence data.

Soft agar colony formation assay: 10,000 cells in exponential growth phase were mixed with 2 ml 0.6% (w/v) agar and transferred into one well of a 6-well tissue culture plate. Once agar was solidified, 2 ml fresh DMEM medium was added to the wells with agar, and the plate was incubated in a regular tissue culture incubator. Medium was replaced every 4 days. After 12 day incubation, DMEM medium was replaced with 1 ml of 12 mM 3-(4,5-dimethylthiazol-2-yl)-2,5-diphenyltetrazolium bromide (MTT). Following 10 minutes incubation with MTT, the images of colonies were acquired using a Nikon TE-100 microscope (Melville, N.Y.).

Detecting Bax insertion into mitochondria and cytochrome c release: Mitochondria were isolated from Bak$^{-/-}$Bax$^{-/-}$ MEF cells as described previously (42). Purified mitochondria were resuspended in 12 mM HEPES (pH7.5), 1.7 mM Tris-HCl (pH7.5), 100 mM KCl, 140 mM mannitol, 23 mM sucrose, 2 mM $KH_2PO_4$, 1 mM $MgCl_2$, 0.67 mM EGTA, and 0.6 mM EDTA supplemented with protease inhibitors (Complete, Roche Diagnostics, Indianapolis, Ind.). Following incubation with compound 106 and different recombinant Bcl-2 proteins at 30° C. for 1 hour, mitochondrial vesicles were resuspended in 100 µl 100 mM $Na_2CO_3$ (pH 11.3) and put on ice for 30 minutes to remove proteins loosely associated with mitochondria. Treated mitochondrial vesicles were centrifuged at 10,000×g for 10 minutes, and vesicles were dissolved in 1 x SDS PAGE loading buffer. Proteins in the vesicle fractions were detected by western blot. Cytochrome c release experiments were carried out as described previously (45). Tom 40 was used as a loading control.

Cell death analysis and Chou-Talalay synergism assay: Cell viability was measured by propidium iodide exclusion using flow cytometry (FACSCalibur, Becton Dickinson) as described previously. The synergistic effect between compound 106 and carboplatin or ABT-737 on cell viability was determined by Chou-Talalay median dose effect assay. $IC_{50}$ of compound 106, carboplatin, and ABT-7373 on a tumor cell line was first determined. Different combinations of drugs at a fixed ratio higher or lower than their $IC_{50}$ values were added to cells. After incubation for the indicated time, cell viability was examined and Fa was calculated as the ratio between the cell death levels of drug-treated cells and those of untreated control cells. Combination index (CI) was determined by the CompuSyn software (Biosoft, Cambridge, UK).

Caspase assay: Caspase-3/7 activities were measured using a Caspase-Glo assay kit (Promega, Madison, Wis., USA). In this assay, the proluminescent substrate containing the amino acid sequence Asp-Glu-Val-Asp (DEVD) is cleaved by activated caspase-3/7, resulting in the release of a luciferase substrate (aminoluciferin) and the production of luminescent signal. Briefly, 24 hours before the treatment, cells were plated in white-walled 96-well plates. At the indicated time points following the treatment of various molecules, cells were mixed with CellTiter-Glo reagent and the luminescence was quantified by a Gemini EM microplate spectrofluorometer (Molecular Devices, Sunnyvale, Calif.) according to the manufacturer's protocols. Data were presented as relative fluorescence units (RFUs) versus time (RFU/min).

Transplanted tumor studies: Eight-week old C57BL/6 female mice (Jackson Laboratories, Bar Harbor, Me.) were inoculated subcutaneously (s.c.) with $1\times10^6$ Lewis Lung Carcinoma tumor cells on the right flank. Mice were examined daily to monitor for side effects of tumor development and the resultant tumors were measured with dull edged Vernier calipers ($V=L\times W^2/2$). Fourteen days after inoculation, the tumor size reached around 200 mm$^3$. 30 animals with size-matched tumors were divided into two groups (control and compound 106 groups). DMSO or 40 mg/kg compound 106 dissolved in DMSO was administered intraperitoneally each day for 13 days. At the end of the experiments, tumors were excised for histological H&E staining and TUNEL labeling, which were carried out by IHCtech (Aurora, Colo.) using standard protocols. The slides were scanned by a ScanScope CS digital slide scanner (Aperio; Vista, Calif.) according to the manufacturer's protocols and analyzed by cellSens digital imaging software (Olympus; Center Valley, Pa.).

EXAMPLES

Example 1

Small Molecules Induce Bax-Dependent but not Bak-dependent Apoptosis

The present inventors hypothesized that small molecules that bind to the Bax hydrophobic groove might cause the dislocation of the Bax membrane anchoring region from the binding groove with subsequent insertion of Bax into mitochondrial membranes. Lead compounds for different protein targets were successfully discovered by virtual screening, a computational approach employing databases of small molecules targeted to the three-dimensional structure of a protein. Preliminary virtual screening experiments using the Bax NMR structure showed that there is a sufficient cavity for a small molecule to fit into the Bax hydrophobic groove. Importantly, this cavity consists of amino acids essential for its interaction with the Bax carboxyl-terminal transmembrane region. Using this information, the present inventors screened ~11 million small molecules for binding to the identified pocket in the Bax hydrophobic groove. The inventors obtained 46 high-score molecules that fit into this hydrophobic groove (FIGS. 1A-1B).

The inventors tested candidate agents by first determining whether cytotoxicity was dependent on Bax but not on Bak. Bax$^{-/-}$Bak$^{-/-}$ murine embryonic fibroblast (MEF) cell lines stably re-expressing only Bax or Bak were established (FIG. 3). Re-expressed Bax and Bak showed similar activities to mediate apoptosis induced by a panel of classic chemotherapeutic drugs (FIGS. 30A-30E). Among the newly identified 46 agents, 21 molecules failed to affect the viability of all cell types, 8 molecules killed all cell types, including Bax$^{-/-}$Bak$^{-/-}$ MEFs, and 11 molecules induced similar levels of cell death in both Bak-expressing and Bax-expressing MEFs. Importantly, 6 molecules displayed cytotoxic activities in Bax-expressing cells, but not in Bak-expressing cells, among which compound 106 exhibited the highest Bax- and dose-dependent cytotoxicity (FIG. 2). Specifically, compound 106 induced significant cell death and caspase 3/7 activation in Bax-expressing cells but not in vector control cells or cells expressing only Bak, indicating that compound 106 is sufficient to trigger cell apoptosis in a Bax-dependent fashion (FIGS. 4-5).

Example 2

Compound 106 Affects Bax Protein Stability and Activates Bax in vitro

The Bax carboxyl-terminal membrane anchoring region is normally sequestered in an inhibitory hydrophobic groove of Bax, preventing its insertion into mitochondrial and other organelle membranes. Thus, the dislocation of the Bax membrane anchoring region from the binding groove will lead to its conformation change.

To investigate whether lead compound 106 was able to activate Bax, the inventors first studied its effects on Bax protein stability in vitro by differential scanning fluorimetry, which can be used to screen small molecules for binding to purified proteins with binding typically influencing the thermal stability of the proteins. When purified recombinant Bax protein (30 μM) was incubated with various doses of compound 106 (90-450 μM), melting temperature (Tm) of Bax protein decreased as the concentration of compound 106 increased, suggesting that Bax conformation is altered by compound 106 in vitro (FIGS. 6-7). In contrast, two compounds displaying no cytotoxicity (678 and 714) failed to alter the Tm of Bax protein, demonstrating that Bax conformation was specifically altered by compound 106 (FIGS. 31-36).

To detect the alteration of Bax protein conformation by compound 106 that leads to Bax activation in vitro, the inventors purified mitochondria from Bax$^{-/-}$13 k$^{-/-}$MEF cells and incubated them with Bax protein, the BH3-only Bcl-2 protein tBid, and various concentrations of compound 106. Like the well-documented Bax activator tBid, compound 106 induced Bax insertion in mitochondria in a dose-dependent fashion (FIG. 8). Furthermore, the inventors carried out experiments to examine the effects of compound 106 on mitochondrial membrane permeabilization, a hallmark of apoptosis. Isolated mitochondria from Bax$^{-/-}$Bak$^{-/-}$ MEF cells were incubated with various purified Bcl-2 proteins and compound 106, and the amount of cytochrome c in both the supernatant (released fraction) and the pellet (mitochondrial fraction) was detected by western blot (FIG. 9). Similar to tBid, compound 106 induced Bax-dependent cytochrome c release. Importantly, the activity of compound 106 on mitochondrial membrane permeability was also regulated by the anti-apoptotic Bcl-2 protein Bcl-x$_L$ in the same fashion as tBid. When various concentrations of compound 106 were incubated with mitochondria purified from Bak re-expressing MEF cells, tBid but not compound 106, induced cytochrome c release, providing more evidence that compound 106 targets Bax but not Bak (FIG. 10). Overall, these data indicate that compound 106, just like the BH3-only Bcl-2 protein tBid, is able to activate Bax in vitro.

Example 3

Cytotoxicity of Compound 106 Depends on Oncogenic Transformation

To systematically investigate how oncogenic transformation influences the cytotoxicity of the Bax-activating compound, the inventors studied two pairs of untransformed MEFs and their isogenic counterparts transformed by expressing the oncogenes K-ras and E1A: one pair of cells expressed all Bcl-2 proteins (wild-type, WT) and another pair was deficient in expression of Bax and Bak (Bax$^{-/-}$ Bak$^{-/-}$, DKO) (FIG. 11). Soft agar colony formation assays indicated that both transformed WT and Bax$^{-/-}$ Bak$^{-/-}$ cells were able to proliferate in an anchorage-independent fashion but untransformed cells did not form colonies (FIGS. 12). Following treatment with compound 106, only wild-type transformed cells underwent highest levels of apoptosis compared with the other three cell lines, indicating that compound 106 preferentially induces cell apoptosis in transformed cells (FIGS. 13-14). To provide more evidence for the specificity of the lead compound on transformed cells, the inventors carried out experiments using normal human bronchia/tracheal epithelial (NHBE) cells and their counterparts immortalized and transformed sequentially by the telomerase catalytic subunit, SV40 large T antigen and an oncogenic ras allele (H-ras V12). This is a well-defined epithelial cell malignant transformation system with relevance to human lung cancer. No change in Bax expression was observed in transformed NHBE compared with primary NHBE (FIG. 15). Similar to MEF cells, upon treatment with compound 106, transformed NHBE underwent higher levels of apoptotic cell death compared with their untransformed counterparts (FIGS. 16-17).

Example 4

Compound 106 Induces Bax-dependent Tumor Cell Apoptosis

To characterize cytotoxicity of compound 106, the inventors examined its cytotoxic effects on various tumor cell lines. Compound 106 induced apoptotic cell death in the murine Lewis Lung Carcinoma (LLC), human non-small cell lung carcinoma A549 cells and PANC-1 human pancreatic carcinoma in a dose-dependent fashion (FIGS. 18-19). To further explore the dependency of Bax expression on compound 106 cytotoxicity in human tumor cells, Bax expression was stably reduced in A549 cells (FIG. 20). Less compound 106-induced apoptotic cell death was observed in A549 cells with decreased Bax expression than cells expressing a control shRNA vector (FIGS. 21-22). In contrast, the reduction of Bax expression did not affect killing activities of the chemotherapeutic drugs carboplatin and vincristine (FIGS. 37A-37B). Furthermore, the inventors also studied the effect of compound 106 on colorectal carcinoma line HCT116 with or without Bax expression. In support of the notion that its cytotoxicity on tumor cell depends on Bax expression, compound 106 induced more apoptotic cell death in Bax-expressing HCT116 tumor cells than in corresponding cells lacking Bax expression in a dose-dependent fashion (FIGS. 23-25). In addition, the absence of Bax expression did not affect killing activities of carboplatin and vincristine (FIG. 37C).

Example 5

Figure 26A:
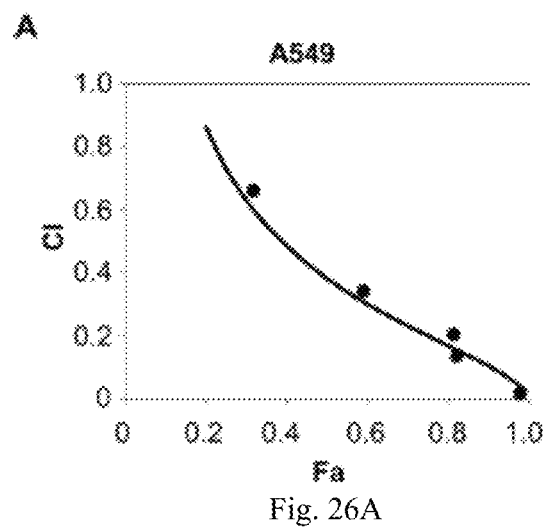
FIGS. 26A-26D plot treatment of indicated cells with combinations of compound 106 with carboplatin (FIGS. 26A-26B), and with ABT-737 (FIGS. 26C-26D). Combination indices (CI) are plotted versus fractional activity (Fa).

Compound 106 Functions Synergistically with Carboplatin or ABT-737 to Induce Human Tumor Cell Death To explore the potential of compound 106 functioning in combination chemotherapy, the inventors investigated whether compound 106 sensitizes tumor cells to die following simultaneous treatment with a chemotherapeutic drug. Carboplatin is currently used to treat non-small-cell lung cancer and human pancreatic cancer. To investigate whether the cytotoxic effects of compound 106 and carboplatin on human tumor cells were synergistic, the inventors carried out median-effect analysis using the Chou-Talalay method. After 48 hours of treatment, the cell death levels of A549 and PANC-1 cells treated with various concentrations of compound 106 and carboplatin at a constant dose ratio were measured, and the combination index (CI) values were determined. As shown in FIG. 26A, in the range of tested drug concentrations, CI values were smaller than 1, indicating that compound 106 and carboplatin exhibited synergistic cytotoxic effects on A549 cells and PANC-1 cells.

Figure 26B:
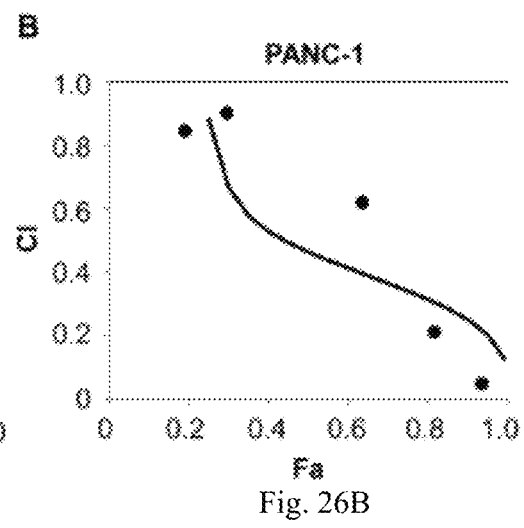
Figure 26C:
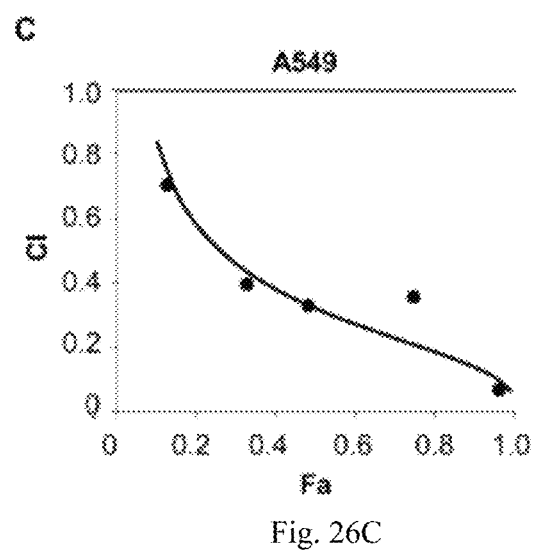
Figure 26D:
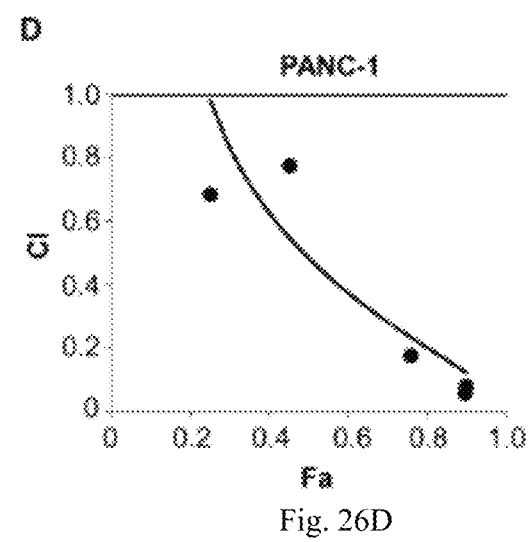

To further explore the therapeutic potential of compound 106, the inventors studied the cytotoxicity of compound 106 along with the Bcl-2/Bcl-$x_L$ inhibitor TUNEL. Various combinations of compound 106 and ABT-737 at a constant dose ratio showed synergistic activities of the two drugs on A549 and PANC-1 cells (FIG. 26B). These data indicate that activating Bax along with inhibiting anti-apoptotic Bcl-2 proteins synergistically induces human tumor cell death, suggesting that the Bax activator might serve as a component of chemotherapy regimens.

Example 6

Compound 106 Inhibits Lung Tumor Growth and Induces Tumor Cell Apoptosis in vivo To determine whether cell death-inducing activity of the Bax activator is relevant in vivo, the inventors implanted Lewis Lung Carcinoma (LLC) cells into mice and examined the effects of compound 106 on the growth of established LLC tumors. As shown in FIG. 27, tumor masses of compound 106-treated mice increased much more slowly than those of the control group during the period of drug administration, indicating that compound 106 exhibited anti-tumor activity as a single-agent. To demonstrate that inhibition of tumor growth was the result of apoptosis, established LLC tumors from mice with or without compound 106 treatment were analyzed with Terminal deoxynucleotidyl Transferase Bioten-dUTP Nick End Labeling (TUNEL) (FIG. 28). The percentage of TUNEL-positive cells was higher in tumors from compound106-treated mice than DMSO-treated mice, suggesting that apoptotic cell death is involved in the cytostatic activity of compound 106 in vivo (FIG. 29).

Any reference cited herein is hereby incorporated by reference in its entirety into the application, whether specifically incorporated or not.

REFERENCES

1. Adams, J. M. and S. Cory. 2007. Bcl-2-regulated apoptosis: mechanism and therapeutic potential. Curr. Opin. Immunol. 19:488-496.
2. Azzoli, C. G., M. G. Kris, and D. G. Pfister. 2007. Cisplatin versus carboplatin for patients with metastatic non-small-cell lung cancer—an old rivalry renewed. J. Natl. Cancer Inst. 99:828-829.
3. Bleicken, S., M. Classen, P. V. Padmavathi, T. Ishikawa, K. Zeth, H. J. Steinhoff, and E. Bordignon. 2010. Molecular details of Bax activation, oligomerization, and membrane insertion. J. Biol. Chem. 285: 6636-6647.
4. Bose, P., A. C. Klimowicz, E. Kornaga, S. K. Petrillo, T. W. Matthews, S. Chandarana, A. M. Magliocco, N.

T. Brockton, and J. C. Dort. 2012. Bax expression measured by AQUAnalysis is an independent prognostic marker in oral squamous cell carcinoma. BMC. Cancer 12:332.
5. Certo, M., G. M. Del, V, M. Nishino, G. Wei, S. Korsmeyer, S. A. Armstrong, and A. Letai. 2006. Mitochondria primed by death signals determine cellular addiction to antiapoptotic BCL-2 family members. Cancer Cell 9:351-365.
6. Chipuk, J. E. and D. R. Green. 2008. How do BCL-2 proteins induce mitochondrial outer membrane permeabilization? Trends Cell Biol. 18:157-164.
7. Chou, T. C. 2010. Drug combination studies and their synergy quantification using the Chou-Talalay method. Cancer Res. 70:440-446.
8. Czabotar, P. E., D. Westphal, G. Dewson, S. Ma, C. Hockings, W. D. Fairlie, E. F. Lee, S. Yao, A. Y. Robin, B. J. Smith, D. C. Huang, R. M. Kluck, J. M. Adams, and P. M. Colman. 2013. Bax crystal structures reveal how BH3 domains activate Bax and nucleate its oligomerization to induce apoptosis. Cell 152:519-531.
9. Danial, N. N. and S. J. Korsmeyer. 2004. Cell death: critical control points. Cell 116:205-219.
10. Dawson, S. J., N. Makretsov, F. M. Blows, K. E. Driver, E. Provenzano, Q. J. Le, L. Baglietto, G. Seyeri, G. G. Giles, C. A. McLean, G. Callagy, A. R. Green, I. Ellis, K. Gelmon, G. Turashvili, S. Leung, S. Aparicio, D. Huntsman, C. Caldas, and P. Pharoah. 2010. BCL2 in breast cancer: a favourable prognostic marker across molecular subtypes and independent of adjuvant therapy received. Br. J. Cancer 103:668-675.
11. Dewson, G., S. Ma, P. Frederick, C. Hockings, I. Tan, T. Kratina, and R. M. Kluck. 2012. Bax dimerizes via a symmetric BH3:groove interface during apoptosis. Cell Death. Differ. 19:661-670.
12. Evan, G. I. and K. H. Vousden. 2001. Proliferation, cell cycle and apoptosis in cancer. Nature 411:342-348.
13. Fesik, S. W. 2005. Promoting apoptosis as a strategy for cancer drug discovery. Nat.Rev.Cancer 5:876-885.
14. Gavathiotis, E., D. E. Reyna, J. A. Bellairs, E. S. Leshchiner, and L. D. Walensky. 2012. Direct and selective small-molecule activation of proapoptotic BAX. Nat. Chem. Biol. 8:639-645.
15. Gavathiotis, E., M. Suzuki, M. L. Davis, K. Pitter, G. H. Bird, S. G. Katz, H. C. Tu, H. Kim, E. H. Cheng, N. Tjandra, and L. D. Walensky. 2008. BAX activation is initiated at a novel interaction site. Nature 455:1076-1081.
16. Grange, F., T. Petrella, M. Beylot-Barry, P. Joly, M. d'Incan, M. Delaunay, L. Machet, M. F. Avril, S. Dalac, P. Bernard, A. Carlotti, E. Esteve, B. Vergier, P. Dechelotte, E. Cassagnau, P. Courville, P. Saiag, L. Laroche, M. Bagot, and J. Wechsler. 2004. Bcl-2 protein expression is the strongest independent prognostic factor of survival in primary cutaneous large B-cell lymphomas. Blood 103:3662-3668.
17. Hanahan, D. and R. A. Weinberg. 2011. Hallmarks of cancer: the next generation. Cell 144:646-674.
18. Hardwick, J. M. and R. J. Youle. 2009. SnapShot: BCL-2 proteins. Cell 138:404, 404.
19. Kaelin, W. G., Jr. 2005. The concept of synthetic lethality in the context of anticancer therapy. Nat. Rev. Cancer 5:689-698.
20. Keith, C. T., A. A. Borisy, and B. R. Stockwell. 2005. Multicomponent therapeutics for networked systems. Nat. Rev. Drug Discov. 4:71-78.
21. Kim, H., M. Rafiuddin-Shah, H. C. Tu, J. R. Jeffers, G. P. Zambetti, J. J. Hsieh, and E. H. Cheng. 2006. Hierarchical regulation of mitochondrion-dependent apoptosis by BCL-2 subfamilies. Nat. Cell Biol. 8:1348-1358.
22. Kim, H., H. C. Tu, D. Ren, O. Takeuchi, J. R. Jeffers, G. P. Zambetti, J. J. Hsieh, and E. H. Cheng. 2009. Stepwise activation of BAX and BAK by tBID, BIM, and PUMA initiates mitochondrial apoptosis. Mol. Cell 36:487-499.
23. Kuwana, T., M. R. Mackey, G. Perkins, M. H. Ellisman, M. Latterich, R. Schneiter, D. R. Green, and D. D. Newmeyer. 2002. Bid, Bax, and lipids cooperate to form supramolecular openings in the outer mitochondrial membrane. Cell 111:331-342.
24. Lambert, J. M., P. Gorzov, D. B. Veprintsev, M. Soderqvist, D. Segerback, J. Bergman, A. R. Fersht, P. Hainaut, K. G. Wiman, and V. J. Bykov. 2009. PRIMA-1 reactivates mutant p53 by covalent binding to the core domain. Cancer Cell 15:376-388.
25. Letai, A. 2005. BCL-2: found bound and drugged! Trends Mol. Med. 11:442-444.
26. Letai, A. 2009. Puma strikes Bax. J. Cell Biol. 185:189-191.
27. Lindsten, T., A. J. Ross, A. King, W. X. Zong, J. C. Rathmell, H. A. Shiels, E. Ulrich, K. G. Waymire, P. Mahar, K. Frauwirth, Y. Chen, M. Wei, V. M. Eng, D. M. Adelman, M. C. Simon, A. Ma, J. A. Golden, G. Evan, S. J. Korsmeyer, G. R. MacGregor, and C. B. Thompson. 2000. The combined functions of proapoptotic Bcl-2 family members bak and bax are essential for normal development of multiple tissues. Mol. Cell 6:1389-1399.
28. Lovell, J. F., L. P. Billen, S. Bindner, A. Shamas-Din, C. Fradin, B. Leber, and D. W. Andrews. 2008. Membrane binding by tBid initiates an ordered series of events culminating in membrane permeabilization by Bax. Cell 135:1074-1084.
29. Nguyen, M., R. C. Marcellus, A. Roulston, M. Watson, L. Serfass, S. R. Murthy Madiraju, D. Goulet, J. Viallet, L. Belec, X. Billot, S. Acoca, E. Purisima, A. Wiegmans, L. Cluse, R. W. Johnstone, P. Beauparlant, and G. C. Shore. 2007. Small molecule obatoclax (GX15-070) antagonizes MCL-1 and overcomes MCL-1-mediated resistance to apoptosis. Proc. Natl. Acad. Sci. U.S.A 104:19512-19517.
30. Ni, C. T., K. A. Sarosiek, T. T. Vo, J. A. Ryan, A. Tammareddi, V. G. Moore, J. Deng, K. C. Anderson, P. Richardson, Y. T. Tai, C. S. Mitsiades, U. A. Matulonis, R. Drapkin, R. Stone, D. J. Deangelo, D. J. McConkey, S. E. Sallan, L. Silverman, M. S. Hirsch, D. R. Carrasco, and A. Letai. 2011. Pretreatment mitochondrial priming correlates with clinical response to cytotoxic chemotherapy. Science 334:1129-1133.
31. Niesen, F. H., H. Berglund, and M. Vedadi. 2007. The use of differential scanning fluorimetry to detect ligand interactions that promote protein stability. Nat.Protoc. 2:2212-2221.
32. Olberding, K. E., X. Wang, Y. Zhu, J. Pan, S. N. Rai, and C. Li. 2010. Actinomycin D synergistically enhances the efficacy of the BH3 mimetic: ABT-737 by downregulating Mcl-1 expression. Cancer Biol. Ther. 10:918-929.
33. Oltersdorf, T., S. W. Elmore, A. R. Shoemaker, R. C. Armstrong, D. J. Augeri, B. A. Belli, M. Bruncko, T. L. Deckwerth, J. Dinges, P. J. Hajduk, M. K. Joseph, S. Kitada, S. J. Korsmeyer, A. R. Kunzer, A. Letai, C. Li, M. J. Mitten, D. G. Nettesheim, S. Ng, P. M. Nimmer, J. M. O'Connor, A. Oleksijew, A. M. Petros, J. C. Reed, W. Shen, S. K. Tahir, C. B. Thompson, K. J. Tomaselli, B. Wang, M. D. Wendt, H. Zhang, S. W. Fesik, and S. H. Rosenberg. 2005. An inhibitor of Bcl-2 family proteins induces regression of solid tumours. Nature 435:677-681.

34. Pozzan, A. 2006. Molecular descriptors and methods for ligand based virtual high throughput screening in drug discovery. Curr. Pharm. Des 12:2099-2110.

35. Ryan, J. A., J. K. Brunelle, and A. Letai. 2010. Heightened mitochondrial priming is the basis for apoptotic hypersensitivity of CD4+ CD8+ thymocytes. Proc. Natl. Acad. Sci. U.S.A 107:12895-12900.

36. Soejima, K., W. Fang, and B. J. Rollins. 2003. DNA methyltransferase 3b contributes to oncogenic transformation induced by SV40T antigen and activated Ras. Oncogene 22:4723-4733.

37. Stewart, M. L., E. Fire, A. E. Keating, and L. D. Walensky. 2010. The MCL-1 BH3 helix is an exclusive MCL-1 inhibitor and apoptosis sensitizer. Nat. Chem. Biol. 6:595-601.

38. Suzuki, M., R. J. Youle, and N. Tjandra. 2000. Structure of Bax: coregulation of dimer formation and intracellular localization. Cell 103:645-654.

39. Vogler, M., D. Dinsdale, M. J. Dyer, and G. M. Cohen. 2009. Bcl-2 inhibitors: small molecules with a big impact on cancer therapy. Cell Death.Differ. 16:360-367.

40. Walensky, L. D. and E. Gavathiotis. 2011. BAX unleashed: the biochemical transformation of an inactive cytosolic monomer into a toxic mitochondrial pore. Trends Biochem. Sci. 36:642-652.

41. Wang, G., Z. Nikolovska-Coleska, C. Y. Yang, R. Wang, G. Tang, J. Guo, S. Shangary, S. Qiu, W. Gao, D. Yang, J. Meagher, J. Stuckey, K. Krajewski, S. Jiang, P. P. Roller, H. O. Abaan, Y. Tomita, and S. Wang. 2006. Structure-based design of potent small-molecule inhibitors of anti-apoptotic Bcl-2 proteins. J. Med. Chem. 49 : 6139-6142.

42. Wang, X., K. E. Olberding, C. White, and C. Li. 2011. Bcl-2 proteins regulate ER membrane permeability to luminal proteins during ER stress-induced apoptosis. Cell Death. Differ. 18:38-47.

43. Wei, M. C., W. X. Zong, E. H. Cheng, T. Lindsten, V. Panoutsakopoulou, A. J. Ross, K. A. Roth, G. R. MacGregor, C. B. Thompson, and S. J. Korsmeyer. 2001. Proapoptotic BAX and BAK: a requisite gateway to mitochondrial dysfunction and death. Science 292: 727-730.

44. Wells, J. A. and C. L. McClendon. 2007. Reaching for high-hanging fruit in drug discovery at protein-protein interfaces. Nature 450:1001-1009.

45. White, C., C. Li, J. Yang, N. B. Petrenko, M. Madesh, C. B. Thompson, and J. K. Foskett. 2005. The endoplasmic reticulum gateway to apoptosis by Bcl-X(L) modulation of the InsP3R. Nat. Cell Biol. 7:1021-1028.

46. Xiros, N., P. Papacostas, T. Economopoulos, G. Samelis, E. Efstathiou, E. Kastritis, H. Kalofonos, A. Onyenadum, D. Skarlos, A. Bamias, H. Gogas, D. Bafaloukos, E. Samantas, and P. Kosmidis. 2005. Carboplatin plus gemcitabine in patients with inoperable or metastatic pancreatic cancer: a phase II multicenter study by the Hellenic Cooperative Oncology Group. Ann. Oncol. 16:773-779.

47. Yip, K. W. and J. C. Reed. 2008. Bcl-2 family proteins and cancer. Oncogene 27:6398-6406.

48. Youle, R. J. and A. Strasser. 2008. The BCL-2 protein family: opposing activities that mediate cell death. Nat. Rev. Mol. Cell Biol. 9:47-59.

49. Zhang, L., J. Yu, B. H. Park, K. W. Kinzler, and B. Vogelstein. 2000. Role of BAX in the apoptotic response to anticancer agents. Science 290:989-992.

50. Zhang, Z., W. Zhu, S. M. Lapolla, Y. Miao, Y. Shao, M. Falcone, D. Boreham, N. McFarlane, J. Ding, A. E. Johnson, X. C. Zhang, D. W. Andrews, and J. Lin. 2010. Bax forms an oligomer via separate, yet interdependent, surfaces. J. Biol. Chem. 285:17614-17627.

Instances of the Present Invention

The present invention can be further described according to the following instances:

Instance 1. A method of treating cancer in a human or animal patient in need thereof, comprising administering to the patient an effective amount of at least one compound or a pharmaceutically-acceptable salt thereof that has been shown in silico to bind to the hydrophobic groove of Bax.

Instance 2. A method of inhibiting the growth of tumor cells in a human or animal patient in need thereof, comprising administering to the patient an effective amount of at least one compound or a pharmaceutically-acceptable salt thereof that has been shown in vitro to cause Bax-dependent apoptosis in the tumor cells.

Instance 3. A method of inhibiting the growth of tumor cells in vitro comprising exposing the tumor cells to at least one compound or a pharmaceutically-acceptable salt thereof that has been shown in silico to bind to the hydrophobic groove of Bax, in conditions that would otherwise promote the growth of the tumor cells.

Instance 4. The methods of any one of instances 1-3, wherein the at least one compound is chosen from: (i) 1-{[5-(3,4-dimethylbenzyl)-1-(3-methoxybenzyl)-4,5,6,7-tetrahydro-1H-pyrazolo[4,3-c]pyridin-3-yl]carbonyl}-3-piperidinol (ZINC14750348 or compound 106); (ii) 1-{1-[(1-ethyl-3,5-dimethyl-1H-pyrazol-4-yl)methyl]-3-piperidinyl}-4-(4-methoxyphenyl)piperazine (ZINC20110124); (iii) 6-(4-(methylthio)phenyl)-2-(pyridin-3-ylmethyl)-2,3,4,6-tetrahydro-1H-benzo[4,5]imidazo[1,2-a][1,3,5]triazino[1,2-c][1,3,5]triazine (ZINC 13638227); (iv) 5-amino-N-(1-benzyl-3-piperidinyl)-2-(2-methoxyphenyl)-1-methyl-1H -benzimidazole-7-carboxamide (ZINC 12150973); (v) 5-(4-fluorophenyl)-2-[[4-(2-methoxyphenyl)piperazin-1-yl]methyl]-4-(oxolan-2-ylmethyl)-1,2,4-triazole-3-thione (ZINC 16076241); and (vi) 4-(1,3-benzodioxol-5-ylacetyl)-1-isobutyl-6-(3-pyridinylmethoxy)-1,4-diazepan-2-one (ZINC 14531256).

Instance 5. A method of treating cancer in a human or animal patient in need thereof, comprising administering to the patient an effective amount of at least one compound or a pharmaceutically-acceptable salt thereof, wherein the compound has the structure:

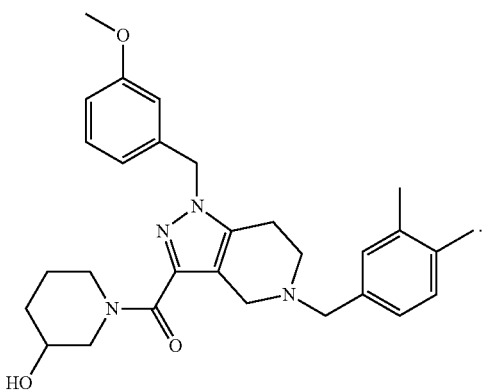 [SMILES: COc1cccc(Cn2nc(C(=O)N3CCCC(O)C3)c3c2CCN(Cc2ccc(C)c(C)c2)C3)c1]

Instance 6. A method of treating cancer in a human or animal patient in need thereof, comprising administering to the patient an effective amount of at least one compound or a pharmaceutically-acceptable salt thereof, wherein the compound has the structure:

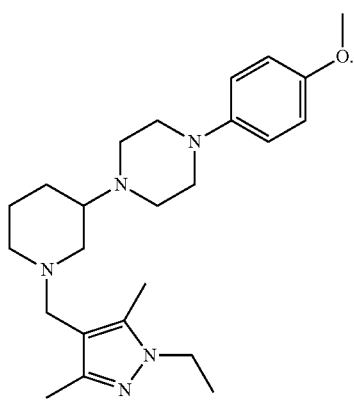 [SMILES: CCn1nc(C)c(CN2CCCC(N3CCN(c4ccc(OC)cc4)CC3)C2)c1C]

Instance 7. A method of treating cancer in a human or animal patient in need thereof, comprising administering to the patient an effective amount of at least one compound or a pharmaceutically-acceptable salt thereof, wherein the compound has the structure:

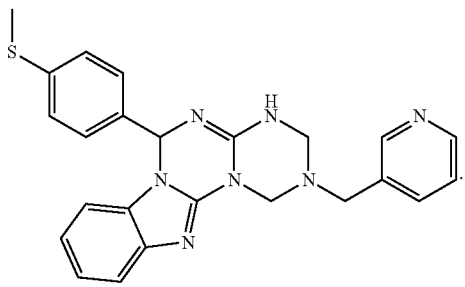 [SMILES: CSc1ccc(C2N=C3NCN(Cc4cccnc4)CN3c3nc4ccccc4n32)cc1]

Instance 8. A method of treating cancer in a human or animal patient in need thereof, comprising administering to the patient an effective amount of at least one compound or a pharmaceutically-acceptable salt thereof, wherein the compound has the structure:

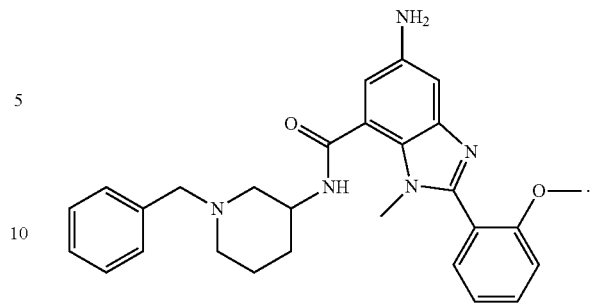

Instance 9. A method of treating cancer in a human or animal patient in need thereof, comprising administering to the patient an effective amount of at least one compound or a pharmaceutically-acceptable salt thereof, wherein the compound has the structure:

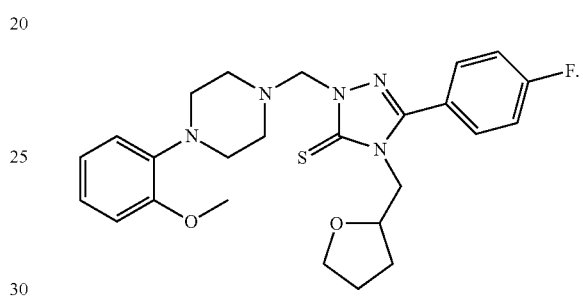

Instance 10. A method of treating cancer in a human or animal patient in need thereof, comprising administering to the patient an effective amount of at least one compound or a pharmaceutically-acceptable salt thereof, wherein the compound has the structure:

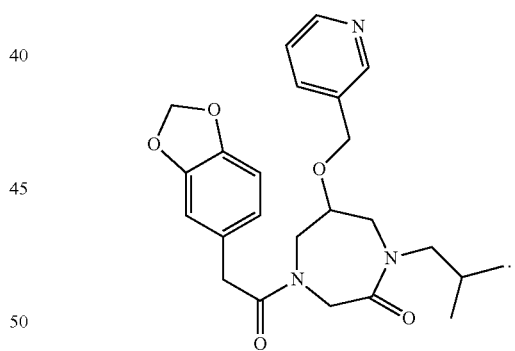

Instance 11. The method of any one of instances 1-10, further comprising administering to the patient (instances 1-2 and 4-10) or exposing to the tumor cells (instance 3) at least one additional anti-cancer agent.

Instance 12. The method of instance 11, wherein the at least one additional anti-cancer agent is chosen from carboplatin, ABT-737, doxorubicin, actinomycin D, etoposide, vincristine, or combinations of two or more thereof.

Instance 13. The method of instance 12, wherein the at least one additional anti-cancer agent is carboplatin.

Instance 14. The method of instance 12, wherein the at least one additional anti-cancer agent is ABT-737.

Instance 15. The method of any one of instances 1-14, wherein the at least one compound does not induce Bak-dependent apoptosis.

What is claimed:

1. A pharmaceutical composition comprising:
an effective amount of 1-{[5-(3,4-dimethylbenzyl)-1-(3-methoxybenzyl)-4,5,6,7-tetrahydro-1H-pyrazolo[4,3-c]pyridin-3-yl]carbonyl}-3-piperidinol, at least one pharmaceutically-acceptable salt thereof, or a combination thereof, and
at least one pharmaceutically-acceptable excipient.

2. A method of inducing the death of Bax-expressing tumor cells in a human or animal patient in need thereof, comprising administering to the patient an effective amount of a compound having the structure 1-{[5-(3,4-dimethylbenzyl)-1-(3-methoxybenzyl)-4,5,6,7-tetrahydro-1H-pyrazolo[4,3-c]pyridin-3-yl]carbonyl}-3-piperidinol, at least one pharmaceutically-acceptable salt thereof, or a combination thereof.

3. The method of claim 2, wherein the compound does not cause Bak-dependent apoptosis in vitro.

4. The method of claim 2, further comprising administering to the patient an effective amount of at least one additional anti-cancer agent.

5. The method of claim 4, wherein the at least one additional anti-cancer agent is chosen from carboplatin, ABT-737, doxorubicin, actinomycin D, etopiside, vincristine, and combinations of two or more thereof.

6. The method of claim 4, wherein the at least one additional anti-cancer agent is carboplatin.

7. The method of claim 4, wherein the at least one additional anti-cancer agent is ABT-737.

* * * * *